(12) United States Patent
Flegel et al.

(10) Patent No.: US 7,005,276 B1
(45) Date of Patent: Feb. 28, 2006

(54) NUCLEIC ACID MOLECULES CORRELATED WITH THE RHESUS WEAK D PHENOTYPE

(75) Inventors: Willy A. Flegel, Dieburg (DE); Franz F. Wagner, Ulm (DE)

(73) Assignee: DRK Blutspendedienst Baden-Württember GGmbH, (DE)

( * ) Notice: Subject to any disclaimer, the term of this patent is extended or adjusted under 35 U.S.C. 154(b) by 0 days.

(21) Appl. No.: 09/600,714

(22) PCT Filed: Dec. 18, 1998

(86) PCT No.: PCT/EP98/08319

§ 371 (c)(1),
(2), (4) Date: Oct. 4, 2000

(87) PCT Pub. No.: WO99/37763

PCT Pub. Date: Jul. 29, 1999

(30) Foreign Application Priority Data

Jan. 23, 1998 (EP) .................................. 98101203

(51) Int. Cl.
*C12P 21/02* (2006.01)
*C12N 1/20* (2006.01)
*C12N 15/70* (2006.01)
*C07H 21/04* (2006.01)
*C07H 21/02* (2006.01)

(52) U.S. Cl. ............... 435/69.1; 435/252.3; 435/320.1; 435/810; 536/23.1; 536/23.5

(58) Field of Classification Search ............... 536/23.1, 536/23.5; 435/69.1, 69.6, 91.1, 252.3, 320.1, 435/810, 69, 252

See application file for complete search history.

(56) References Cited

U.S. PATENT DOCUMENTS 6,200,802 B1 * 3/2001 Greene et al.

OTHER PUBLICATIONS

LeVan et al, Blood 83: 3098-3100, 1994.*
Salvignol et al, Biochem Genet 32: 201-221.*
Cherif-Zahar et al Proc. Natl. Sci. U.S.A. 87: 6243-6247.*
Sambrook et al in Molecular Cloning, 1989, Cold Spring Harbor Laboratory, CSH, NY, Ch. 11 & 17.*
Wallace et al in Methods Enzymol 152: 432-439, 1987.*
Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Skolnick et al, From genes to protein structure and function: novel applications of computational approaches in the genomic-er Jan., 2000, TIBTECH 18: 34-39.*
Rouillac et al (Am J Hematol 49(1): 87-8, May 1995.*
Legler et al, Transfusion 38(5): 434-40, May 1998.*

* cited by examiner

*Primary Examiner*—Christina Chan
*Assistant Examiner*—Phuong Huynh
(74) *Attorney, Agent, or Firm*—Pillsbury Winthrop Shaw Pittman

(57) ABSTRACT

The present invention relates to novel nucleic acid molecules encoding a Rhesus D antigen contributing to the weak D phenotype which are characterized by one or a combination of missense mutations or by a gene conversion involving exons 6 to 9 of the RHD and RHCE genes. The present invention further relates to vectors comprising the nucleic acid molecules of the invention, to hosts transformed with said vectors, to proteins encoded by said nucleic acid molecules and to methods of producing such polypeptides. The fact that missense mutations and the conversion referred to above can be directly correlated to the weak D phenotype has a significant impact on the routine testing of blood samples. For example, oligonucleotides and antibodies can now be designed that generally allow the detection of weak D phenotypes in a sample. Such oligonucleotides, antibodies as well as a variety of diagnostic methods all fall within the scope of the present invention. RhD antigens encoded by the novel nucleic acid molecules may be used for the characterization, standardization and quality control of monoclonal and polyclonal anti-D antisera. Finally, the invention relates to a kit useful for testing for the presence of weak D phenotypes.

10 Claims, 7 Drawing Sheets

Figure 1:
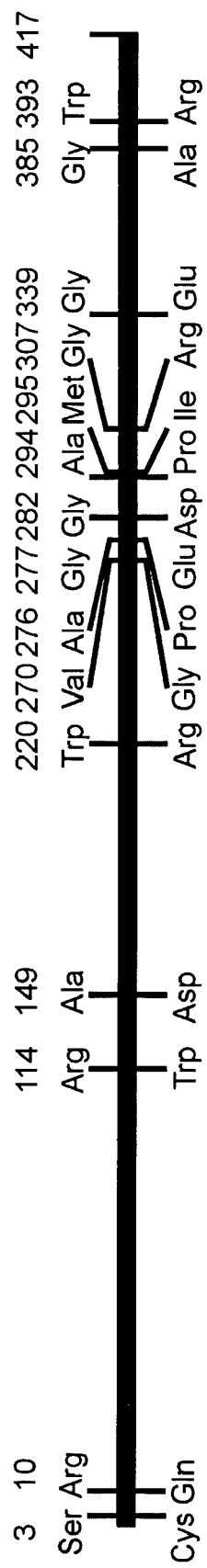

```
  1
ATG AGC TCT AAG TAC CCG CGG TCT GTC CGG CGC TGC CTG CCC CTC TGG GCC CTA ACA CTG   60
Met Ser Ser Lys Tyr Pro Arg Ser Val Arg Arg Cys Leu Pro Leu Trp Ala Leu Thr Leu
 1                   10                            20

GAA GCA GCT CTC ATT CTC TTC TAT TTT TTT ACC CAC TAT GAC GCT TCC TTA GAG GAT      120
Glu Ala Ala Leu Ile Leu Phe Tyr Phe Phe Thr His Tyr Asp Ala Ser Leu Glu Asp
              30                            40

CAA AAG GGG CTC GTG GCA TCC TAT CAA GTT GGC CAA GAT CTG ACC GTG ATG GCG GCC ATT  180
Gln Lys Gly Leu Val Ala Ser Tyr Gln Val Gly Gln Asp Leu Thr Val Met Ala Ala Ile
          50                            60

GGC TTG GGC TTC CTC ACC TCG AGT TTC CGG AGA CAC AGC AGC AGT GTG GCC TTC AAC      240
Gly Leu Gly Phe Leu Thr Ser Ser Phe Arg Arg His Ser Ser Ser Val Ala Phe Asn
              70                            80

CTC TTC ATG CTG GCG CTT GGT GTG CAG TGG GCA ATC CTG CTG GAC GGC TTC CTG AGC CAG  300
Leu Phe Met Leu Ala Leu Gly Val Gln Trp Ala Ile Leu Leu Asp Gly Phe Leu Ser Gln
          90                           100

TTC CCT TCT GGG AAG GTC GTC ATC ACA CTG TTC AGT ATT CGG CTG GCC ACC ATG AGT GCT  360
Phe Pro Ser Gly Lys Val Val Ile Thr Leu Phe Ser Ile Arg Leu Ala Thr Met Ser Ala
             110                           120

TTG TCG GTG CTG ATC TCA GTG GAT GCT GTC TTG GGG AAG GTC TTG GGT AAG GTG CAG TTG GCG CAG TTG GTG  420
Leu Ser Val Leu Ile Ser Val Asp Ala Val Leu Gly Lys Val Asn Leu Ala Gln Leu Val
             130                           140
```

FIG. 2A

```
GTG ATG GTG CTG GTG GAG GTG ACA GCT TTA GGC AAC CTG AGG ATG GTC ATC AGT AAT ATC
Val Met Val Leu Val Glu Val Thr Ala Leu Gly Asn Leu Arg Met Val Ile Ser Asn Ile
                  440                         460                          420
                                          150                                160

TTC AAC ACA GAC TAC CAT ATG AAC ATG CAC ATC TAC GTG TTC GCA GCC TAT TTT GGG
Phe Asn Thr Asp Tyr His Met Asn Met His Ile Tyr Val Phe Ala Ala Tyr Phe Gly
                  500                         520                      540
              Phe Asn Thr Asp Tyr His Met Asn Met                        180
                                          170

CTG TCT GTG GCC TGG TGC CTG CCA AAG CCT CTA CCC GAG GGA ACG GAG GAT AAA GAT CAG
Leu Ser Val Ala Trp Cys Leu Pro Lys Pro Leu Pro Glu Gly Thr Glu Asp Lys Asp Gln
                  560                         580                      600
                                          190                                200

ACA GCA ACG ATA CCC AGT TTG TCT GCC ATG CTG GGC GCC CTC TTC TTG TGG ATG TTC TGG
Thr Ala Thr Ile Pro Ser Leu Ser Ala Met Leu Gly Ala Leu Phe Leu Trp Met Phe Trp
                  620                         640                      660
                                          210                                220

CCA AGT TTC AAC TCT GCT CTG CTG AGA AGT CCA ATC GAA AGG AAG AAT GCC GTG TTC AAC
Pro Ser Phe Asn Ser Ala Leu Leu Arg Ser Pro Ile Glu Arg Lys Asn Ala Val Phe Asn
                  680                         700                      720
                                          230                                240

ACC TAC TAT GCT GTA GCA GTC AGC GTG GTG ACA GCC ATC TCA GGG TCA TCC TTG GCT CAC
Thr Tyr Tyr Ala Val Ala Val Ser Val Val Thr Ala Ile Ser Gly Ser Ser Leu Ala His
                  740                         760                      780
                                          250                                260

CCC CAA GGG AAG ATC AGC AAG ACT TAT GTG CAC AGT GCG GTG TTG GCA GGA GGC GTG GCT
Pro Gln Gly Lys Ile Ser Lys Thr Tyr Val His Ser Ala Val Leu Ala Gly Gly Val Ala
                  800                         820                      840
                                          270                                280
```

FIG. 2B

```
GTG GGT ACC TCG TGT CAC CTG ATC CCT TCT CCG TGG CTT GCC ATG GTG CTG GGT CTT GTG      900
Val Gly Thr Ser Cys His Leu Ile Pro Ser Pro Trp Leu Ala Met Val Leu Gly Leu Val
                                         290                                   300

GCT GGG CTG ATC TCC GTC GGG GGA GCC AAG TAC CTG CCG GGG TGT TGT AAC CGA GTG CTG      960
Ala Gly Leu Ile Ser Val Gly Gly Ala Lys Tyr Leu Pro Gly Cys Cys Asn Arg Val Leu
                                         310                                   320

GGG ATT CCC CAC AGC TCC ATC ATG GGC TAC AAC TTC AGC TTG CTG GGT CTG CTT GGA GAG     1020
Gly Ile Pro His Ser Ser Ile Met Gly Tyr Asn Phe Ser Leu Leu Gly Leu Leu Gly Glu
                                         330                                   340

ATC ATC TAC ATT GTG CTG CTG GTG CTT GAT ACC GTC GGA GCC GGC AAT GGC ATG ATT GGC     1080
Ile Ile Tyr Ile Val Leu Leu Val Leu Asp Thr Val Gly Ala Gly Asn Gly Met Ile Gly
                                         350                                   360

TTC CAG GTC CTC CTC AGC ATT GGG GAA CTC AGC TTG CTA AAT CTT AAA ATA TGG AAA GCA     1140
Phe Gln Val Leu Leu Ser Ile Gly Glu Leu Ser Leu Asn Leu Lys Ile Trp Lys Ala Leu
                                         370                                   380

GGT CTC CTG ACA GGT TTG CTC CTC CTA AAT CTT AAA ATA TGG AAA GCA CCT CAT GAG GCT AAA     1200
Gly Leu Leu Thr Gly Leu Leu Leu Leu Asn Leu Lys Ile Trp Lys Ala Pro His Glu Ala Lys
                                         390                                   400

TAT TTT GAT GAC CAA GTT TTC TGG AAG TTT CCT CAT TTG GCT GTT GGA TTT TAA     1251
Tyr Phe Asp Asp Gln Val Phe Trp Lys Phe Pro His Leu Ala Val Gly Phe ***
                                         410                         417
```

FIG. 2C

```
                10           20           30           40         50
RHCE  AGCCACTTCA   ACGTTTTGAG   TCTCAGTGGC   CTCATCTGTA   AAGTGAGAAT  650
RHD   ----------   ----------   ----------   --------G-   ----.-----

RHCE  TAAGAGATGG   TGCATGTAAA   GTGCTTAACG   GGGAGTAAAT   GGTAGGCAAA  700
RHD   ----------   ----------   ----------   ----------   ----------

RHCE  CATTAGCTGC   TGCTATTAGT   ACAGAGAGAC   AATGGTGTGT   GTGAGTCTTG  750
RHD   ----------   ----------   -A--------   G---------   ----------

RHCE  TGGGCAGAGA   TGGGTGAGAG   GGGAGACAAA   ACAAGTTCTC   ATGATGATGG  800
RHD   ----------   ----------   ----------   ----------   ----------

RHCE  GGGCAGGGGG   TCCAGCTGGT   GGTGTCGGAG   GGAAGTCTGG   ACAGACCAGT  850
RHD   ---A----C-   ----------   ----------   ----------   ---------*

RHCE  GGTGGGGCTC   GGGTGGGAGG   CACTGGGGGG   GCTGGAGTGG   AAAGAATGTG  900
RHD   ----------   ----------   ----------   ----------   ---------*

RHCE  GCCACAGATG   ACAGCTTCAC   AGCAGAATTC   AGTGCTAAGA   GGAAGTGAGT  950
RHD   ----------   ----------   ----------   ----------   ---------*

RHCE  GGCCATGAGT   TCCATGGTGA   CAGAAAGTCT   AAGACACCTA   GCAAGGCAGG  1000
RHD   ----------   ----------   ----------   ------C---   ---------|
```

*FIG. 3A*

```
RHCE  AGTGGGTGTC  AGCTCAGGGA  AGCTCAGAGG  CTAAACCTAG  GTGAGAGCTG  1050
RHD   ----------  -A--------  ---C------  -------T--  ----------

RHCE  AGGGTGTCAG  ATAAGAGCAA  GGCAAGGCTC  CGGTTCTGGA  GTAGTGAAGG  1100
RHD   ----------  ----------  ----------  --------C-  ----------

RHCE  ACATAGCAGA  GCTATAACCC  AGGAACAAGG  CCCAGCTTAT  TGGAACTGGG  1150
RHD   ----------  -----G----  ----------  ----------  -----A----

RHCE  ACCAGTCACA  CAGGGTGGCA  CAGGCACCAA  GTAGCCAATA  ATAATAAATAA  1200
RHD   C---------  ----------  ----------  ----------  ----------

RHCE  AAACAATAAC  AATGATTTAT  TGTCATTGGG  CATTTATTCA  TGTTCTATGC  1250
RHD   ----------  -------G--  -------C--  ----------  ----------

RHCE  CAGACACTGG  ACTAAGAGCT  TTATATGTGG  AAACTCATTT  AATCCTTACA  1300
RHD   ----------  G---------  ----------  ----------  ----------
```

*FIG. 3B*

NUCLEIC ACID MOLECULES CORRELATED WITH THE RHESUS WEAK D PHENOTYPE

This application is a 371 of PCT EP/98/08319, filed Dec. 12, 1998, which claims priority to EP 98101203.2, filed Jan. 23, 1998.

The present invention relates to novel nucleic acid molecules encoding a Rhesus D antigen contributing to the weak D phenotype which are characterized by one or a combination of missense mutations or by a gene conversion involving exons 6 to 9 of the RHD and RHCE genes. The present invention further relates to vectors comprising the nucleic acid molecules of the invention, to hosts transformed with said vectors, to proteins encoded by said nucleic acid molecules and to methods of producing such polypeptides. The fact that missense mutations and the conversion referred to above can be directly correlated to the weak D phenotype has a significant impact on the routine testing of blood samples. For example, oligonucleotides and antibodies can now be designed that generally allow the detection of weak D phenotypes in a sample. Such oligonucleotides, antibodies as well as a variety of diagnostic methods all fall within the scope of the present invention. RhD antigens encoded by the novel nucleic acid molecules may be used for the characterization, standardization and quality control of monoclonal and polyclonal anti-D antisera. Finally, the invention relates to a kit useful for testing for the presence of weak D phenotypes.

The Rhesus D antigen (ISBT 004.001; RH1) carried by the RhD protein is the most important blood group antigen determined by a protein. It is still the leading cause for the hemolytic disease of the newborn (Mollison et al. 1993). About 0.2% to 1% of whites have red cells with a reduced expression of the D antigen (weak D, formerly D$^u$) (Mourant et al. 1976; Stratton, 1946; Wagner et al. 1995). A small fraction of weak D samples is explained by qualitatively altered RhD proteins, called partial D (Salmon et al. 1984) and frequently caused by RHD/RHCE hybrid alleles (recently reviewed in Huang, 1997). Another fraction is caused by the suppressive effects of Cde haplotypes in trans position (Ceppellini et al. 1955). These weak D likely possess the normal RHD allele, because the carriers' parents and children express often a normal RhD antigen density. Such weak D show only a minor reduction of RhD C antigen expression, were loosely called "high grade D" and typed today often as normal RhD, because of the increased sensitivity of monoclonal anti-D antibodies.

The majority of moderately to strongly weakened antigen D are due to genotype(s) located either at the Rhesus genes' locus itself or closeby, because the weak D expression is inherited along with the RhD phenotype (Stratton, 1946). Besides the mere quantitative reduction, no qualitative differences could be discerned in the RhD antigen of this most prevalent type of weak D. Two recent studies addressed the molecular cause of the prevalent weak D phenotypes. Both groups, Rouillac et al. (1996) and Beckers et al. (1997), performed RT-PCR and found no mutations when sequencing of RHD cDNA in weak D samples. Using semi-quantitative RT-PCR, Rouillac et al. (1996) reported reduced steady-state levels of RHD transcripts in weak D samples and disclosed, that their observations provided direct evidence of an only quantitative difference in RhD between normal and weak D red blood cells. In a similar approach, Beckers et al. (1995 and 1997), however, found no differences in the amounts of RHD transcripts and excluded an excess of splice variants (Kajii et al. 1995), whose products may be inadequately or not at all incorporated in the red cell membrane (Beckers et al. 1997). They concluded that weak D is not caused by regulatory defects of the transcription process and proposed unidentified regulatory genes or factors involved in the Rh-related complex as possible causes of weak D. Hence, while the mechanism of weak D expression remained equivocal, no molecular cause was established. Screening of random weak D samples by PCR for RHD specific polymorphisms confirmed PCR amplification patterns representative for a normal RHD allele (Avent et al. 1997b; Legler et al. 1997). However, evidence was accumulating that very few weak D not known to represent partial D, may carry structurally abnormal RHD alleles: Four of 44 weak D in England lacked RHD specific intron 4 PCR amplicons (Avent et al. 1997b) and one out of 94 weak D in Northern Germany lacked RHD specific exon 5 PCR amplicons (Legler et al. 1997). In the latter sample, the nucleotide T at position 667 was substituted by the RHCE specific G coding for a F223V amino acid substitution (TJ Legler and A Humpe, personal communications).

Thus, aberrant alleles were observed only in a small fraction of weak D phenotypes rendering the possibility unlikely that these changes at the molecular level were indeed responsible for the general phenomenon of the weak D phenotype; see also Aubin et al. 1997; Avent et al. 1997b; Fukumori et el., 1997; Huang, 1997; Issitt and Telen, 1996; Roubinet et al., 1996. Consequently, the combined prior art failed to hitherto provide an conveniently applicable and reliable means to detect the weak Rhesus D phenotype in a sample.

Accordingly, the technical problem underlying the present invention was to establish such a means as well as methods that can conveniently and widely be employed in the analysis of the Rhesus weak D phenotype.

The solution to said technical problem is achieved by providing the embodiments characterized in the claims. Thus, the present invention relates to a nucleic acid molecule encoding a Rhesus D antigen contributing to or indicative of the weak D phenotype, said nucleic acid molecule carrying at least one missense mutation, as compared to the wild type Rhesus D antigen, in its transmembrane and/or intracellular regions.

In accordance with the present invention, the term "contributing to the weak D phenotype" implies an active role of the mutation which may be caused by an amino acid exchange whereas the term "indicative of the weak D phenotype" does not necessarily imply such a role but may also refer to a silent mutation. Such a silent mutation may, for example, occur in conjunction with other mutations such as missense mutations which are addressed in more detail herein below.

In accordance with the present invention, it was found that the observed missense mutations are not only associated with, but truly caused a reduced RhD protein integration into the red blood cells' membranes. Thus, by the present invention it is demonstrated that (i) weak D alleles evolved independently in the different haplotypes, each distinct event being associated with a change in the RhD coding sequence; (ii) no sample occurred with a normal coding sequence despite the observation of 16 different alleles in 164 samples; and (iii) type and distribution of the observed nucleotide substitutions was not compatible with the null hypotheses of random changes.

The finding that missense mutations in RHD led to reduced D antigen expression, fitted into the current model of RhD membrane integration; see Table 7. Both Rh proteins occur in a complex with the Rh50 protein, which can be joined by several additional proteins, like LW, CD47, and glycophorin B (Huang, 1997). The expression of the whole Rh complex depends on the integrity of at least one Rh protein (JP Cartron, oral presentation at the ISBT/DGTI conference, Frankfurt, September 1997) and the Rh50 protein (Cherif-Zahar et al. 1996). Subtle structural changes in the Rh50 protein caused by missense mutations are sufficient to prevent the expression of the Rh complex (Cherif-Zahar et al. 1996). Likewise, such subtle structural changes in the RhD protein appear to also affect the expression of the Rh complex involving RhD.

Based on the distribution and kind of amino acid substitutions, a general picture of the relationship of RhD structure and RhD expression can now be established: All amino acid substitutions in weak D are located in the intracellular or transmembrane parts of the RhD protein where the alignment was carried out in accordance with the above mentioned current model (see Table 7). Known RHD alleles with exofacial substitutions (Avent et al. 1997a; Jones et al. 1997; Liu et al. 1996; Rouillac et al. 1995) were discovered by virtue of their partial D antigen, but may display discrete (DNU and $D^{VII}$) to moderate ($D^{II}$, DHR and DHMi) reductions in RhD expression (Flegel and Wagner, 1996; Jones et al. 1997; Jones et al. 1996). Most substitutions reported in accordance with this invention were nonconservative and the introduced amino acids, in particular proline, likely disrupted the secondary or tertiary structure. Two weak D alleles (type 2 and 11) were associated with conservative substitutions indicating that the involved amino acid regions at positions 295 and 385 were very important for an optimal RhD membrane integration. In two alleles (type 4 and type 14), parts of exon 4 and 5 were substituted by the corresponding parts of the RHCE gene. Similar exchanges occurred in $D^{VI}$ type I and $D^{VI}$ type II that exhibited a considerably reduced RhD protein expression (Jones et al. 1996), too. Previous paradoxical observations can be explained, if the N152T substitution in exon 3 is considered to facilitate the membrane integration: (i) $D^{IIIa}$ (Huang et al. 1997), differing from weak D type 4 by the N152T substitution only, has a normal RhD antigen density (Jones et al. 1996), and (ii) $D^{IIIc}$, $D^{IVa}$, and $D^{VI}$ type III harbouring the N152T substitution have enhanced antigen densities (Flegel et al. 1997; Jones et al. 1996) compared to their appropriate controls (normal RhD and $D^{VI}$ type II).

Several phenotypes with weak D expression, like $D^{VI}$, $D^{V}$, DBT, some $D^{IV}$ and DFR, were recognized long ago as separate entities by their carriers' propensity to produce anti-D (Lomas et al. 1994; Tippett and Sanger, 1977; Tippett and Sanger, 1962). These phenotypes were subsequently confirmed and grouped by distinct reaction patterns with monoclonal anti-D (Lomas et al. 1993; Lomas et al. 1989; Scott, 1996). A serologic classification of most weak D phenotypes, however, has not been successful, because they lacked a consistent reaction pattern with monoclonal anti-D and their carriers seemed not prone to anti-D immunization (Moore, 1984). There was even no defined borderline between normal D and weak D (Agre et al. 1992; Moore, 1984; Nelson et al. 1995). Nevertheless, variability of the RhD antigen density (antigens per cell) in weak D phenotypes (Hasekura et al. 1990; Jones et al. 1996; Nelson et al. 1995; Nicholson et al. 1991; Tazzari et al. 1994; Wagner, 1994) and rare aberrant patterns in RHD PCR (Avent et al. 1997b; Legler et al. 1997) did not exclude an underlying molecular diversity. The present invention for the first time allows for the convenient classification of weak D and for the unambiguous correlation of distinct alleles with clinical data. In conjunction with previously defined rare RHD alleles, the exact molecular definition of most phenotypes with reduced D antigen density has now become possible. In the case that patients carrying particular molecular types of weak D were prone to develop anti-D, the classification made possible by the present invention will help to guide a Rhesus negative transfusion policy. The availability of weak D samples that are characterized in regard to molecular structure and RhD antigen densities will promote the quality assurance of anti-D reagents. They should reliably type probands as RhD positive, whose RhD proteins are not prone to frequent anti-D immunization (Wagner et al. 1995). Therefore, the use of RhD negative red blood cell units for transfusions to weak D patients, which has been justified by a presumed potential for anti-D immunization, can finally be reduced to a minimum, which can be scientifically deduced.

Additionally, it was found in accordance with the invention that the mutations cluster in certain stretches of the Rhesus D polypeptide. Further, a gene conversion correlating with the weak D phenotype was detected. Thus, the invention also relates to a nucleic acid molecule encoding a Rhesus D antigen contributing to or indicative of the weak D phenotype, said nucleic acid molecule (a) carrying at least one missense mutation, as compared to the wild type Rhesus D antigen, in amino acid positions 2–16, 114–149, 179–225 or/and 267 to 397 with the proviso that said D antigen does not carry a single missense mutation leading to a substitution of phenylalanine in amino acid position 223 by valine or of threonine in position 283 by isoleucine; or (b) carrying a gene conversion involving exons 6 to 9 which are replaced by the corresponding exons of the RHCE gene.

All the missense mutations found in accordance with the present invention and located in the above regions are associated with the transmembrane region or the intracellular portion of the polypeptide when the above indicated current model of RhD is employed. However, when different models are employed, the mutations associated with the weak D phenotype may also be found in the extracellular regions. The above regions also comprise amino acid positions which are located in the extracellular regions when the current model is applied. Said positions might also be mutated and correlatable with the weak D phenotype. Such mutations also fall within the scope of the application.

In addition to the missense mutations, a gene conversion indicative of weak D was identified. Said conversion can be used for diagnostic purposes basically to the same extent as the missense mutations. In accordance with the invention, the breakpoints are determined to be in introns 5 and 9; see also FIG. 3.

The mutants referred to above and further throughout this specification can be conveniently employed for the characterization of monoclonal and polyclonal antibodies used in connection with RhD diagnosis, prophylaxis and treatment. For example, by expressing desired nucleic acid molecules encoding such mutants in a suitable system, reactivity profiles of said antibodies or antisera can be established. The mutants can also be employed for the characterization of monoclonal and polyclonal antibodies that are used as secondary antibodies, for example, anti-globulin and anti-human-globulin antisera.

Preferably, the missense mutation causes an amino acid substitution in position 3, 10, 16, 114, 149, 182, 198, 201, 220, 223, 270, 276, 277, 282, 294, 295, 307, 339, 385 or 393 or a combination of/or involving said substitutions.

This preferred embodiment, besides the single mutations indicated, may comprise a combination of these substitutions. Additionally, it contemplates the possibility that one or more of said substitutions are involved, and additional mutations such as mutations leading to substitutions are present. In accordance with the present invention, it is understood that such additional mutations may be tested for when assessing RhD status in a sample. A finding of such a mutation will allow the person skilled in the art to conclude that other mutations identified in this specification occurring in combination with said first mutation will be present. Accordingly, such embodiments reflecting the detection of additional mutations occurring in combination with the mutations identified in this specification are also comprised by the invention.

In a particularly preferred embodiment of the nucleic acid molecule of the invention, said amino acid substitution in position 3 is from Ser to Cys, in position 10 from Arg to Gin, in position 16 from Trp to Cys, in position 114 from Arg to Trp, in position 149 from Ala to Asp, in position 182 from Ser to Thr, in position 198 from Lys to Asn, in position 201 from Thr to Arg, in position 220 from Trp to Arg, in position 223 from Phe to Val, in position 270 from Val to Gly, in position 276 from Ala to Pro, in position 277 from Gly to Glu, in position 282 from Gly to Asp, in position 294 from Ala to Pro, in position 295 from Met to Ile, in position 307 from Gly to Arg, in position 339 from Gly to Glu, in position 385 from Gly to Ala and in position 393 from Trp to Arg.

In a further preferred embodiment of the nucleic acid molecule of the invention, said missense mutation occurs in nucleotide position 8, 29, 48, 340, 446, 544, 594, 602, 658, 667, 809, 819, 826, 830, 845, 880, 885, 919, 1016, 1154 and 1177 or in a combination of said positions.

Particularly preferred is that said missense mutation in position 8 is from C to G, in position 29 from G to A, in position 48 from G to C, in position 340 from C to T, in position 446 from C to A, in position 544 from T to A, in position 594 from A to T, in position 602 from C to G, in position 658 from T to C, in position 667 from T to G, in position 809 from T to G, in position 819 from G to A, in position 826 from G to C, in position 830 from G to A, in position 845 from G to A, in position 880 from G to C, in position 885 from G to T, in position 919 from G to A, in position 1016 from G to A, in position 1154 from G to C and in position 1177 from T to C.

In the case that combinations of missense mutations are involved in the generation of weak D phenotypes, it is preferred that said combination of substitutions is in positions 182, 198 and 201 and is preferably S182T, K198N, T201R or in position 201 and 223 and is preferably T201R and F223V, or in position 16, 201 and 223 and is preferably W16C, T201 R and F223V.

Most preferably, said combination of missense mutations comprises positions 544, 594 and 602 and is preferably T→A at position 544, A→T at position 594 and C→G at position 602 or comprises positions 602, 667 and 819 and is preferably C→G at position 602, T→G at position 667 and G→A at position 819, or comprises positions 48, 602, 667 and 819 and is preferably G→C at position 48, C→G at position 602, T→G at position 667 and G→A at position 819.

Although the nucleic acid molecule of the invention may be of various origin including (semi) synthetic origin, it is preferred that the nucleic acid molecule is mRNA or genomic DNA. Standard procedures may be employed to obtain any of the above nucleic acids; see, for example, Sambrook, et al., "Molecular Cloning, A Laboratory Manual", $2^{nd}$ ed. 1989, CSH Press, Cold Spring Harbor, N.Y.

The invention also relates to a vector comprising the nucleic acid molecule of the invention.

The vector may be used for propagation and/or expression or may be designed for gene transfer or targeting purposes. Methods of producing such vectors are well known in the art. The same holds true for cloning the nucleic acids of the mutation into said vectors, as well as the propagation of vectors in suitable hosts, etc.

The vector may particularly be a plasmid, a cosmid, a virus or a bacteriophage used conventionally in genetic engineering that comprise the nucleic acid molecule of the invention. Expression vectors derived from viruses such as retroviruses, vaccinia virus, adeno-associated virus, herpes viruses, or bovine papilloma virus, may be used for delivery of the nucleic acid molecules or vector of the invention into targeted cell populations. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

Such vectors may comprise further genes such as marker genes which allow for the selection of said vector in a suitable host cell and under suitable conditions. Preferably, the nucleic acid molecule of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the nucleic acid molecule. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium.

Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used.

As mentioned above, the vector of the present invention may also be a gene transfer or targeting vector. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534–539; Schaper, Circ. Res. 79 (1996), 911–919; Anderson, Science 256 (1992), 808–813; Isner, Lancet 348 (1996), 370–374; Muhlhauser, Circ. Res. 77 (1995), 1077–1086; Wang, Nature Medicine 2 (1996), 714–716; WO94/29469; WO 97/00957 or Schaper, Current Opinion in Biotechnology 7 (1996), 635–640, and references cited therein. The polynucleotides and vectors of the invention may be designed for direct introduction or for introduction via liposomes, or viral vectors (e.g. adenoviral, retroviral) into the call. Preferably, said cell is a germ line cell, embryonic cell, most preferably said cell is a stem cell.

Additionally, the invention relates to a host transformed with the vector of the invention.

Appropriate hosts comprise transgenic animals, cells such as bacteria, yeast cells, animal, preferably mammalian cells, fungal cells or insect cells. Transformation protocols including transfection, microinjection, electroporation, etc., are also well known in the art.

Further, the invention relates to a method of producing a Rhesus D antigen contributing to the weak D phenotype comprising culturing the host of the invention under suitable conditions and isolating the Rhesus D antigen produced.

It is preferred that the antigen is exported into the culture medium where it can be collected according to conventions/methods. The term "culturing" as used in accordance with the present invention also comprises the raising of transgenic animals. Using appropriate vectors constructions and optionally appropriate feeds, the antigen may, e.g., be isolated from milk of, e.g. transgenic cows.

The invention additionally relates to Rhesus D antigen encoded by the nucleic acid molecule of the invention or produced by the method of the invention.

Preferably, the antigen is in the same way post transitionally modified and has the same chemical structure as naturally occurring antigen. Accordingly, said antigen, when produced by the method of the invention, is preferably produced in human cells.

Furthermore, the invention relates to an oligonucleotide hybridizing under stringent conditions to a portion of the nucleic acid molecule of the invention comprising said at least one missense mutation or to the complementary portion thereof or hybridizing to a breakpoint of the gene conversion identified here in the above.

In this embodiment of the invention, it is understood that the oligonucleotides hybridizes directly to the mutated sequence or to the breakpoint. The setting of stringent hybridization conditions is well described, for example, in Sambrook et al, "Molecular Cloning, A Laboratory Handbook" CSH Press, Cold Spring Harbor 1989 or Hames and Higgins, "Nucleic acid hybridization, a practical approach", IRL Press, Oxford (1985). Thus, the detection of the specifically hybridizing sequences will usually require hybridization and washing conditions such as 0.1×SSC, 0.1% SDS at 65°. As is well known, the length of the probe and the composition of the nucleic acid to be determined constitute further parameters of the stringent hybridization conditions. Preferably, the oligonucleotide is a deoxynucleotide. It is further preferred that the oligonucleotide comprises 12 to 50 nucleotides and more preferably 15 to 24 nucleotides. The hybridization to the breakpoint may be under stringent or non-stringent conditions. An example of non-stringent hybridization conditions is hybridization and washing at 50° C. in 4×SSC, 0,1% SDS.

Further, the invention relates to an antibody or an aptamer specifically binding to the Rhesus D antigen of the invention.

The antibody may be tested and used in any serologic technique well known in the art, like agglutionation techniques in tubes, gels, solid phase and capture techniques with or without secondary antibodies, or in flow cytometry with or without immunofluorescence enhancement.

The antibody of the invention may be a monoclonal antibody or an antibody derived from or comprised in a polyclonal antiserum. The term "antibody", as used in accordance with the present invention, further comprises fragments of said antibody such as Fab, F(ab')$_2$, Fv or scFv fragments; see, for example, Harlow and Lane, "Antibodies, A Laboratory Manual" CSH Press 1988, Cold Spring Harbor, N.Y. The antibody or the fragment thereof may be of natural origin or may be (semi) synthetically produced. Such synthetic products also comprises non-proteinaceous as semi-proteinaceous material that has the same or essentially the same binding specificity as the antibody of the invention. Such products may, for example, be obtained by peptidomimetics.

Additionally, the invention relates to an antibody or an aptamer or a phage specifically binding to the wild type Rhesus D antigen or to aberrant D Rhesus antigens but not to the Rhesus D antigen of the invention. The antibody may be tested and used in any serologic technique well known in the art, like agglutionation techniques in tubes, gels and solid phase techniques, capture techniques or flow cytometry with immunofluorescence.

As regards, the definition, testing and origin of the antibody or the aptamer, the same definitions as above apply here.

As regards the term "aberrant Rhesus D antigen", the term comprises prior art missense mutations as well as prior art conversions found in RHD genes and the corresponding antigens.

The term "aptamer" is well known in the art and defined, e.g., in Osborne et al., Curr. Opin. Chem. Biol. I (1997), 5–9 or in Stall and Szoka, Pharm. Res. 12 (1995), 465–483.

Furthermore, the invention relates to a method for testing for the presence of a nucleic acid molecule encoding a Rhesus D antigen contributing to or indicative of the weak D phenotype in a sample comprising hybridizing the oligonucleotide of the invention or an oligonucleotide hybridizing to a nucleic acid molecule encoding a Rhesus D antigen contributing to or indicative of the weak D phenotype, said nucleic acid molecule carrying at least one missense mutation, as compared to the wild type Rhesus D antigen, said missense mutation causing an amino acid substitution in position 223 or 283 which is in position 223 preferably from Phe to Val and in position 283 preferably from Thr to Ile, said missense mutation further preferably occurring in nucleotide position 667 or 848 wherein most preferably said mutation in position 667 is form T to G and in position 848 from C to T under stringent conditions to nucleic acid molecules comprised in the sample obtained from a human and detecting said hybridization.

Preferably, the method of the invention further comprises digesting the product of said hybridization with a restriction endonuclease or subjecting the product of said hybridization to digestion with a restriction endonuclease and analyzing the product of said digestion.

This preferred embodiment of the invention allows by convenient means, the differentiation between an effective hybridization and a non-effective hybridization. For example, if the wild type Rhesus D antigen comprises an endonuclease restriction site, the hybridized product will be cleavable by an appropriate restriction enzyme whereas a mutated sequence will yield no double-stranded product or will not comprise the recognizable restriction site and, accordingly, will not be cleaved. Alternatively, the hybridizing oligonucleotide may only hybridize to the mutated sequence. In this case, only a hybrid comprising the mutated sequence, but not the wild type sequence, will be cleaved by the appropriate restriction enzyme. The analysis of the digestion product can be effected by conventional means, such as by gel electrophoresis which may be optionally combined by the staining of the nucleic acid with, for example, ethidium bromide. Combinations with further techniques such as Southern blotting are also envisaged.

Detection of said hybridization may be effected, for example, by an anti-DNA double-strand antibody or by employing a labeled oligonucleotide. Conveniently, the method of the invention is employed together with blotting techniques such as Southern or Northern blotting and related techniques. Labeling may be effected, for example, by standard protocols and includes labeling with radioactive markers, fluorescent, phosphorescent, chemiluminescent, enzymatic labels, etc.

The invention additionally relates to a method of testing for the presence of a nucleic acid molecule encoding a Rhesus D antigen contributing to or indicative of the weak D phenotype in a sample comprising determining the nucleic acid sequence of at least a portion of the nucleic acid molecule of the invention, said portion encoding at least one of said missense mutations or a breakpoint of said gene conversion or a nucleic acid molecule encoding a Rhesus D antigen contributing to or indicative of the weak D phenotype, said nucleic acid molecule carrying at least one missense mutation, as compared to the wild type Rhesus D antigen, said missense mutation causing an amino acid substitution in position 223 or 283 which is in position 223 preferably from Phe to Val and in position 283 preferably from Thr to Ile, said missense mutation further preferably occurring in nucleotide position 667 or 848 wherein most preferably said mutation in position 667 is form T to G and in position 848 from C to T.

Preferably, the method of the invention further comprises, prior to determining said nucleic acid sequence, amplification of at least said portion of said nucleic acid molecule.

Preferably, amplification is effected by polymerase chain reaction (PCR). Other amplification methods such as ligase chain reaction may also be employed.

Furthermore, the invention relates to a method for testing for the presence of a nucleic acid molecule encoding a Rhesus D antigen contributing to or indicative of the weak D phenotype in a sample comprising carrying out an amplification reaction wherein at least one of the primers employed in said amplification reaction is the oligonucleotide of the invention or an oligonucleotide hybridizing to a nucleic acid molecule encoding a Rhesus D antigen contributing to the weak D phenotype, said nucleic acid molecule carrying at least one missense mutation, as compared to the wild type Rhesus D antigen, said missense mutation causing an amino acid substitution in position 223 or 283 which is in position 223 preferably from Phe to Val and in position 283 preferably from Thr to Ile, said missense mutation further preferably occurring in nucleotide position 667 or 848 wherein most preferably said mutation in position 667 is form T to G and in position 848 from C to T and assaying for an amplification product.

The method of the invention will result in an amplification of only the target sequence, if said target sequence carries the or at least one mutation. This is because the oligonucleotide will under preferably stringent hybridization conditions not hybridize to the wild type sequence (with the consequence that no amplification product is obtained) but only to the mutated sequence. Naturally, primer oligonucleotides hybridizing to one or more as one, such as two mutated sequences may be employed in the method of the invention. The latter embodiment may be favorable in cases where combinations of mutations are tested for. It is important to note that not all or none of said mutations are necessarily missense mutations. This may be true for cases where other types of mutations occur in combination with the above missense mutations or with the above gene conversion.

Preferably, in the method of the invention said amplification or amplification reaction is or is effected by the polymerase chain reaction (PCR). Other amplification methods such as ligase chain reaction may also be employed.

Further, the invention relates to a method for testing for the presence of a Rhesus D antigen contributing to or indicative of the weak D phenotype in a sample comprising assaying a sample obtained from a human for specific binding to the antibody or aptamer or phage of the invention or to an antibody or aptamer or phage to a Rhesus D antigen contributing to or indicative of the weak D phenotype and encoded by a nucleic acid molecule carrying at least one missense mutation, as compared to the wild type Rhesus D antigen, said missense mutation causing an amino acid substitution in position 223 or 283 which is in position 223 preferably from Phe to Val and in position 283 preferably from Thr to Ile, said missense mutation further preferably occurring in nucleotide position 667 or 848 wherein most preferably said mutation in position 667 is form T to G and in position 848 from C to T.

Testing for binding may, again, involve the employment of standard techniques such as ELISAs; see, for example, Harlow and Lane, "Antibodies, A Laboratory Manual" CSH Press 1988, Cold Spring Harbor.

The invention also relates to the method of testing a sample for the presence of wild type Rhesus D antigen and the absence of the Rhesus D antigen of the invention comprising assaying a sample obtained from a human for specific binding to the antibody or aptamer or phage of the invention, said antibody or aptamer or phage specifically binding to the wild type Rhesus D antigen or to aberrant D Rhesus antigens but not to the Rhesus D antigen of the invention.

Results obtained in accordance with their method of invention may well be employed in strategies of blood transfusion, as outlined herein above.

Preferably, in the method of the invention said sample is blood, serum, plasma, fetal tissue, saliva, urine, mucosal tissue, mucus, vaginal tissue, fetal tissue obtained from the vagina, skin, hair, hair follicle or another human tissue.

Furthermore, the method of the invention preferably comprises the step of enrichment of fetal cells. This enrichment may be achieved by using appropriate antibodies, lectins or other reagents specifically binding fetal cells or by any technique attempting the differential separation of maternal and fetal cells, like by density gradients. Also preferably, in said method fetal DNA or mRNA from material tissue like peripheral blood, serum or plasma may be extracted, advantageously according to conventional procedures.

In an additional preferred embodiment of the method of the invention, said nucleic acid molecule or proteinaceous material from said sample is fixed to a solid support.

Preferably, said solid support is a chip.

The advantages of chips are well known in the art and need not be discussed herein in detail. These include the small size as well as an easy access of computer based analysis of analytes.

Furthermore, the present invention relates to the use of the nucleic acid molecule of the invention or of a nucleic acid molecule encoding a Rhesus D antigen contributing to or indicative of the weak D phenotype, said nucleic acid molecule carrying at least one missense mutation, as compared to the wild type Rhesus D antigen, said missense mutation causing an amino acid substitution in position 223 or 283 which is in position 223 preferably from Phe to Val and in position 283 preferably from Thr to Ile, said missense mutation further preferably occurring in nucleotide position 667 or 848 wherein most preferably said mutation in position 667 is form T to G and in position 848 from C to T or of a combination thereof for the analysis of a weak Rhesus D phenotype.

The analysis can be effected, for example, on the basis of the methods described herein above.

The invention also relates to the use of the nucleic acid molecule of the invention, the vector of the invention or the Rhesus D antigen of the invention for the assessment of the affinity, avidity and/or reactivity of monoclonal anti-D antibodies or of polyclonal anti-D antisera or of anti-globulin or of anti-human-globulin antisera or of preparations thereof.

The invention also relates to the use of cells, preferably red blood cells, from probands for the assessment of the affinity, avidity and/or reactivity of monoclonal anti-D antibodies or of polyclonal anti-D antisera or of anti-globulin or of anti-human-globulin antisera or of preparations thereof.

Said preparations can be provided according to techniques well known in the art. Said preparations may comprise stabilisators such as albumins, further sodium azide, salt ions, buffers etc. The formulation of the preparation may have an influence on the binding characteristics of the antibodies, as is well known in the art.

For example, in a first step, the Rhesus D gene of a carrier or of a blood donor and its allelic status is analyzed and it is determined whether said gene comprises a mutation that was found in accordance with the present invention. In a second step, said mutation is correlated to a certain RhD antigen density on the surface of red blood cells. Conveniently, said correlation can be established by data provided in the present invention (such as mutations per se) and techniques that are well known in the art (see, e.g. Jones et al. 1996, Flegel and Wagner, 1996). In a third step, the features of an antibody or an antiserum such as reactivity, sensitivity, affinity, avidity, and/or specificity are determined with suitable blood group serological techniques preferably using red blood cells that were molecularly and with respect to the RhD antigen surface density characterized as described in step 2. Such data can be used, for example, in quality controls, standardization, etc.

The invention will be most useful for the characterization, standardization an quality control of monoclonal and polyclonal antisera, preferably anti-D monoclonals or antisera. Further, for example, anti-globulin and anti-human-globulin antisera can be characterized on the basis of the teachings of the present invention. An appropriately characterized anti-D monoclonal antibody can be conveniently used in RhD diagnostics. For example, a suitably characterized monoclonal antibody will be useful in determining the weak D antigen density on the surface of blood cells. Cut-off values for monoclonal antibodies useful in diagnosis can thus be established. This is important for the quality control of antibodies used in RhD diagnosis.

Thus, the invention also relates to a method for the characterization of monoclonal antibodies or polyclonal antisera or of a preparation thereof, said method comprising (a) testing the nucleic acid of sample of a proband for the presence of a mutation as defined in accordance with the invention;

(b) correlating, on the basis of the mutation status and the allelic status of the RHD gene, the nucleic acid with the RhD antigen density on the surface of red blood cells of said proband;

(c) reacting said monoclonal antibodies or polyclonal antisera or said preparation thereof with a cell carrying the RhD antigen on its surface;

(d) characterizing said monoclonal antibodies or polyclonal antisera or said preparation thereof on the basis of the results obtain in step (c).

As regards the term "allelic status", this term describes the possibilities that the RHD alleles in a proband are present in a homozygous, heterozygous or hemizygous state. Also comprised by this term is the possibility that the two alleles carry two different mutations (including the conversion) defined herein above.

In a preferred embodiment of the method of the invention, said characterization comprises the determination of reactivity, sensitivity, avidity, affinity, specificity and/or other characteristics of antibodies and antisera.

Furthermore preferred is a method wherein said cell carrying the RhD antigen on its surface is a red blood cell.

The invention also relates to a method for determining whether a patient in need of a blood transfusion is to be transfused with Rh D negative blood from a donor comprising the step of testing a sample from said patient for the presence of one or more Rh D antigens of the invention, wherein a positive testing for at least one of said antigens is indicative of the need for a transfusion with Rh negative blood. The invention has important implications for devising a transfusion therapy in humans. For example, it can now be conveniently tested whether the patient actually needs a transfusion with a Rh D negative blood or whether such precautions need not be taken.

The transfusion of red blood cells of some molecularly defined subgroups of the weak D phenotype determined by such methods may be immunogenic, if carriers of the wild type Rhesus D antigen, an aberrant D antigen or another weak D type of the invention were transfused by some subgroup of the weak D phenotype. Such carriers, like blood donors, may be determined by previously established methods in the art or by methods established in the invention and subsequently the transfusion of some subgroups of the weak D phenotype may be avoided.

Furthermore, the invention relates to a method for determining whether blood of a donor may be used for transfusion to a patient in need thereof comprising the step of testing a sample from said donor for the presence of one or more Rh D antigens of the invention, wherein a positive testing for at least one or said antigens excludes the transfusion of patients that are typed as having wild type Rh D antigen or (a) weak D type(s) other than the weak D type(s) of said donors.

On the basis of the method of the invention, it is advantageous and desired to avoid transfusion of a patient with weak D typed blood from a donor, if the weak D antigens in both donor and recipient are not totally identical.

The samples referred to in the above recited methods may be samples that are referred to throughout the specification, such as blood, serum, etc.

As regards the guidelines for transfusing a patient on the basis of any of the above recited methods, the utmost care must be taken that suboptimal transfusion policy is avoided. The risk factor is always to be considered by the physician in charge. In all cases, the potential risk for the patient is to be minimized.

The present invention is particularly suitable for establishing criteria which will guide the future strategies in blood transfusion policy. According to the molecular criteria established by the invention, the weak D phenotype can be grouped. Some molecularly defined subgroups of the weak D phenotype determined by such methods may be prone to immunization, if the carriers were transfused with the wild type Rhesus D antigen, an aberrant D antigen or another weak D type of the invention, and may produce an anti-D. Such carriers may be determined by methods established in the invention and subsequently transfused with Rhesus negative blood components, like erythrocyte, thrombocyte and plasma blood units. The majority of carriers with weak D phenotype is by the current art not considered prone to be immunized in such a way by Rhesus D positive blood transfusions and may, hence, by the means established by the invention safely be transfused Rhesus D positive, because of their classification to a distinct weak D type according to the present invention.

The invention also relates to the use of a phage, aptamer, monoclonal antibody or a polyclonal antisera or a preparation thereof as characterized in the present invention for RhD antigen determination.

In a preferred embodiment of said use, said RhD antigen determination is effected in connection with blood group typing.

Furthermore, the invention relates to a preparation comprising the antibody or aptamer or phage of the invention.

The weak D types defined by the invention correlate with certain RhD epitope and RhD antigen densities, i.e. RhD antigens per cell expressed on the red blood cell surface (Flegel and Wagner 1996) (data from few examples are provided in Table 8) Antibodies and preparations thereof may be tested by any standard blood group serology technique with one or more weak D types of the invention. The reactivity, sensitivity, avidity, affinity, specificity and/or other characteristics of antibodies and antisera known in the art may be determined by its reaction with one or more weak D types of the invention under predetermined conditions in standard blood group serology techniques well know in the art. The preparation may be a diagnostic or pharmaceutical preparation.

The pharmaceutical composition of the present invention may further comprise a pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

An antibody and its preparation may be characterized by its reaction or lack of reaction to surfaces with certain RhD epitope densities. For example, antibody preparations may be characterized by agglutinating red blood cells with 1,000 RhD antigens per cell—a RhD antigen density deliberately chosen to be met for quality control purposes.

The invention also relates to treating a pregnant woman being Rhesus D negative or being hemizygous for a mutation defined herein above wherein the child is Rhesus D positive or carries a different mutation defined herein above in a hemizygous state comprising administering anti-D to said woman.

Pregnant women may be currently treated with an anti-D prophylaxis, when a Rhesus negative mother carries a RhD positive fetus. The invention allows the discrimination of an anti-D prophylaxis requirement depending on the status of the mother's and/or the fetus' possessing a RhD protein of the invention. One or more of the RhD proteins of the invention may be prone to immunization of their carriers and, hence, would be indicative for the therapy of the mother. Similarly, one or more RhD proteins of the invention, when carried by the fetus, may be known to be of low immunogenicity to the mother and, hence, would be indicative for the omission of anti-D prophylaxis in difference to current clinical therapy.

The administration can be effected by standard routes and doses which can be defined by the attending physician; Mollison, 1993. Preferably, a monoclonal anti-D or combinations/mixtures of monoclonal anti-Ds is/are administered in doses of 50 μg to or exceeding 500 μg anti-D antibody/antisera for intravenous or intramuscular administration (Bowman, 1998). For the quality control of these anti-D antibodies/antisera, the results and methods provided by the present invention may be advantageously employed.

The present invention also relates to a method of identifying an antibody $V_H$ or $V_L$ chain or a combination thereof or an aptamer specifically binding to a weak D polypeptide of the invention comprising
(a) contacting the weak D polypeptide of the invention with a phage library displaying $V_H$ or $V_L$ chains or combinations thereof on the surface of the phage or with aptamers;
(b) identifying phage or aptamers that bind to said weak D polypeptide; and optionally
(c) repeating steps (a) and (b) one or more times.

The preparation of phage library and the screening/identification of desired antibody (chains) per se is well known in the art and reviewed, for example, in Winter et al., Annu. Rev. Immunol. 12 (1994), 433–455 and references cited therein. Also, aptamers can be prepared and cloned in phage according to conventional protocols. Whereas single $V_H$ or $V_L$ chains may be identified by the method of the invention as binding to the weak D polypeptide of the invention, it is preferred to identify $V_H$-$V_L$ combinations expressed by the phage because this situation resembles the situation of natural antibody binding. By repeating steps (a) and (b) one or more times, better binding specificities may be identified. Protocols for the optimization of binding properties such as affinities, including elution steps for removing bound phage, are well established in the art. For example, once a $V_H$ chain with a convenient binding capacity has been found, $V_L$ chains may be identified that significantly improve the binding capacity of the antibody, e.g. by replacing the $V_L$ chain that was associated with the $V_H$ chain in the first selection step with a more suitable $V_L$ chain.

The invention also relates to a method of identifying a monoclonal antibody specifically binding to a weak D polypeptide/antigen of the invention comprising
(a) contacting the weak D polypeptide of the invention with one or more monoclonal antibodies;
(b) identifying monoclonal antibodies that bind to said weak D polypeptide; and optionally
(c) repeating steps (a) and (b) one or more times.

The invention also relates to a method of identifying an antibody $V_H$ or $V_L$ chain or a combination thereof or an aptamer specifically binding to a weak D polypeptide/antigen of the invention comprising
(a) contacting the weak D polypeptide and
(aa) a second or more weak D weak D polypeptide(s) and/or
(ab) a normal Rhesus D polypeptide
wherein the second or more weak D polypeptide(s) and/or the normal Rhesus D polypeptide are present in a molar mass that is higher, equal or less than the weak D polypeptide of (a) with a phage library displaying $V_H$ or $V_L$ chains or combinations thereof on the surface of the phage or with aptamers;
(b) identifying phage or aptamers that bind to said weak D polypeptide of (a); and optionally
(c) repeating steps (a) and (b) one or more times.

Particularly preferred in step (ab) is that the molar mass of the second weak D polypeptide and the normal Rhesus D polypeptide is higher than that of the weak D polypeptide of (a).

In the case that only one round of selection is employed for the identification (i.e. when step (c) does not apply), it is preferred that the number of weak D polypeptide molecules of (a) is in molar excess over the number of phage particles. The preferred embodiments of the method of identifying an antibody $V_H$ or $V_L$ chain or of a combination thereof or of an aptamer described hereinbefore equally apply to this embodiment of the invention.

The invention also relates to a method of identifying a monoclonal antibody specifically binding to a weak D polypeptide/antigen of the invention comprising
(a) contacting the weak D polypeptide and
(aa) a second or more weak D polypeptide(s) and/or
(ab) a normal D polypeptide
wherein the second or more weak D polypeptide(s) and/or the normal D polypeptide are present in a molar mass that is higher, equal or less than the weak D polypeptide of (a) with one or more monoclonal antibodies;
(b) identifying monoclonal antibodies that bind to said weak D polypeptide of (a); and optionally
(c) repeating steps (a) and (b) one or more times.

Preferably, the weak D polypeptide is exposed on the surface of a cell. An appropriate surface is the surface of an erythrocyte. However, other host cells may be transfected with a vector suitable for expression of the weak D polypeptide and express the same on their surface. Antibodies may also bind to recombinant proteins of or parts of proteins of weak D and purified proteins.

It is further preferred that the polypeptide or host cell is affixed to a solid support. Suitable examples for solid supports are microtiter plates or beads.

In an additionally preferred antibody, subsequent to step (b) or (c), the following step is carried out:
(d) identifying the amino acid sequence of the $V_H$ or $V_L$ chains and/or identifying the nucleic acid sequences encoding said amino acid sequence.

The identification of the amino acid/nucleic acid sequences can be effected according to conventional protocols; see, e.g., Sambrook et al., loc. cit.

Finally, the invention relates to a kit comprising
(a) the oligonucleotide of the invention; and/or
(b) the antibody of the invention;
(c) the aptamer of the invention: and/or
(d) the phage of the invention.

The kit of the invention which may comprise various types of antibodies described herein above, is particularly suitable for the analysis of weak Ds in samples obtained from humans. The components of the kit may be packaged as appropriate. Preferably, different components are packaged in different vials.

The disclosure content of the documents as cited in this specification is herewith incorporated by reference.

The figures show

FIG. 1. Schematic representation of the amino acid variations observed in weak D types with single missense mutations. The affected amino acids of the prevalent normal RhD protein and their positions are shown on top. Their substitutions occurring in the weak D types are shown below the bar.

FIG. 2. The cDNA nucleotide (SEQ ID NO:41) and predicted amino acid sequences of the prevalent allele of the RHD gene. The consensus sequences are shown that are deposited in the EMBL nucleotide sequence data base under the accession number X54534 by Avent et al. and modified as noted in the description (C at 1,036). The positions of the nucleotides and amino acids are indicated by the numbers above and below the sequences, respectively.

FIG. 3. Part of intron 5 of the RHCE and RHD genes. The nucleotide sequence of the RHCE gene is shown (SEQ ID NO:42). Numbers indicate the position relative to the first base of exon 5 in the RHCE gene. Dashes denote nucleotides in the RHD gene (SEQ ID NO:43) that are identical to the RHCE gene. The 5' breakpoint region (178 bp) of the gene conversion characteristic for D category IV type III is indicated by asterisks. The full intron 5 nucleotide sequences are deposited in EMBL/Genbank under accession numbers Z97333 (RHCE) and Z97334 (RHD).

Figure 4:
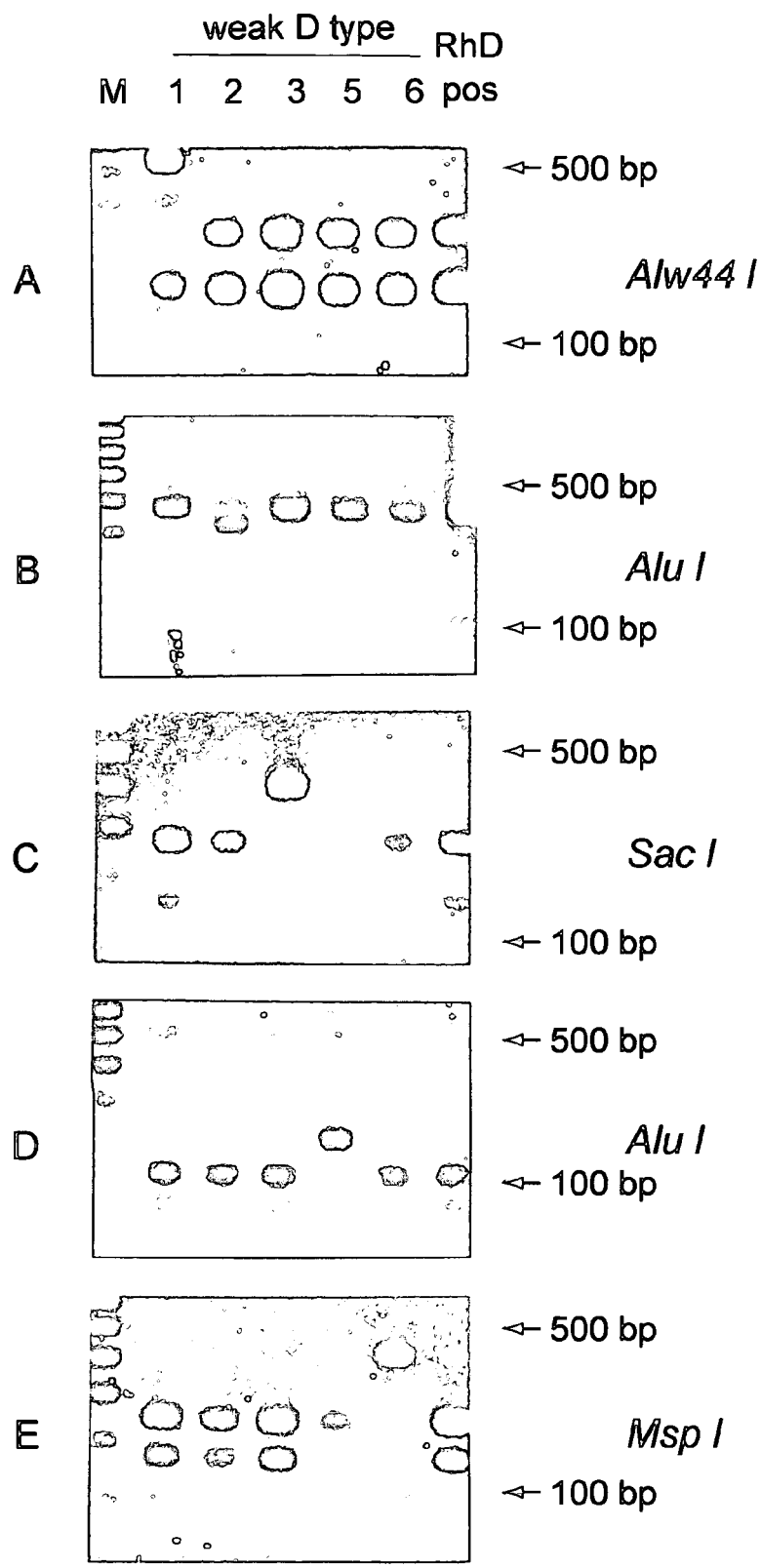

FIG. 4. Detection of weak D types by PCR-RFLP. Four weak D types harboured point mutations that obliterated restriction sites: Weak D type 1 lacks an Alw44 site (Panel A), weak D type 3 a SacI site (Panel C), weak D type 4 an AluI site (Panel D) and weak D type 6 a MspI site (Panel E). In a fifth weak D type, a point mutation introduced a restriction site: Weak D type 2 gained an AluI site (Panel B). On the left side of the gels, 100 bp ladders are shown; the position of the 500 bp and 100 bp fragments are indicated on the right side of the panels. For the PCR reaction of panel A, the largest restriction fragment approximation 3,000 bp is not shown.

The example illustrates the invention.

Example: Molecular Analysis of Samples of the Weak D Phenotype

A method for RHD specific sequencing of the ten RHD exons and their splice sites was developed (Table 1 and 2). In a sequential analysis strategy, blood samples with weak expression of antigen D were checked by this method, PCR-RFLP (Table 3) and RHD PCR-SSP (Gassner et al. 1997). For this purpose, EDTA- or citrate-anticoagulated blood samples were collected from white blood donors and characterized as weak D during donor typing in accordance with published standards ("D" test") (Wissenschaftlicher Beirat der Bundesärztekammer and Bundesgesundheitsamt, 1992) as described (Wagner et al. 1995). D category VI samples were excluded from this study.

Coding sequence of RHD in weak D phenotypes. Sequencing of the ten RHD exons from genomic DNA. DNA was prepared as described previously (Gassner et al. 1997). Nucleotide sequencing was performed with a DNA sequencing unit (Prism dye terminator cycle-sequencing kit with AmpliTaq FS DNA polymerase; ABI 373A, Applied Biosystems, Weiterstadt, Germany). Nucleotide sequencing of genomic DNA stretches representative of all ten RHD exons and parts of the promoter (see below) was accomplished using primers (Table 1) and amplification procedures (Table 2) that obviated the need of subcloning steps.

Control of RHD specificity. RHD exons 3 to 7 and 9 carry at least one RHD specific nucleotide, which was used to verify the RHD origin of the sequences. For exon 1, characteristic nucleotides in the adjacent parts of intron 1 were used (EMBL nucleotide sequence data base accession numbers Z97362 and Z97363). For exon 8, the RHD specificity of the PCR amplification was checked by RHD non-specific sequencing of the informative exon 9, since exons 8 and 9 were amplified as a single PCR amplicon (Table 2). Exon 2 and 10 were amplified in an RHD specific way (Table 2) based on published RHD specific nucleotide sequences used (EMBL nucleotide sequence data base accession numbers U66340 and U66341; Kemp et al. 1996; Le Van Kim et al. 1992); no PCR amplicons were obtained in RhD negative controls. All normal D and weak D samples showed a G at position 654 (Arce et al. 1993) and a C at position 1036 (Le Van Kim et al. 1992), supporting the notion (Cartron, 1996) that the alternatively described C (Le Van Kim et al. 1992) and T (Arce et al. 1993), respectively, were sequencing errors.

Detection of weak D specific mutations by PCR-RFLP and PCR-RFLP. PCR-RFLP as well as RH PCR-SSP (Gassner et al. 1997) were developed or applied to characterize distinct nucleotide substitutions detected in five RHD alleles (see also Tables 3 and 4): The C to G substitution at position 8 led to the loss of a SacI restriction site in amplicons obtained with re01 and re11d (G to A at 29, loss of MspI site, re01/re11 d; C to A at 446, loss of AluI site, rb20d/rb21d, T to G at 809, loss of Alw441 site, rf51/re71; G to C at 1154, introduction of AluI site, re82/re93). Conditions for the rf51/re71 PCR reaction were as shown in Table 2. The rb20d/rb21d reaction was done with non-proofreading Taq-polymerase (Boehringer Mannhaim or Qiagen) with 20 s denaturation at 94° C., 30 s annealing at 60° C. and 30 s extension at 72° C. The other PCR reactions were done with non-proofreading Taq-polymerase with 20 s denaturation at 94° C., 30 s annealing at 55° C. and 1 min extension at 72° C.

Another four RHD alleles were detected by a standard RH PCR-SSP[15]: The RHD(T201R, F223V) and RHD(S182T, K198N, T201R) alleles lacked specific amplicons for RHD exon 4, the RHD(G307R) and RHD(A276P) alleles those for RHD exon 6. For all other weak D types, the authenticity of the point mutations was checked by nucleotide sequencing of independent PCR amplicons.

Sequencing of exons 6 to 9 in $D^{IV}$ type III. In $D^{IV}$ type III exons 6 to 9 were amplified and sequenced using primers that were specific for RHCE and RHD. Therefore, primer re71 (Table 2) was substituted by primer rb7; primer re621 by rb26; and primer re52 by re74.

Sixteen RHD alleles with distinct nucleotide changes coding for amino acid substitutions were identified. (Table 4). One allele represented a typical, yet unpublished, RHD-CE-D hybrid allele dubbed hereby $D^{IV}$ type III. Another allele was DHMi (Liu et al. 1996). Of the remaining 14 alleles, 12 showed single, but distinct previously unknown missense mutations. None of the encoded variant amino acids occurred at the corresponding positions in the RhCE proteins. Two alleles exhibited multiple nucleotide changes typical for the RHCE gene, which were interspersed by RHD specific sequences.

Distribution of weak D alleles in whites. A set of 161 samples with weak expression of antigen D were chosen from random blood donors in South-Western Germany. D category VI samples but no other partial D were excluded by serologic methods. Thus, three samples represented known partial D (DHMi (Liu et al. 1996) and D category IV (Lomas et al. 1989)). Without any exception, all samples could be assigned to distinct RHD alleles with aberrant coding sequences (Table 5). For the purpose of the present invention, it is proposed that the new molecular weak D types should be referred to by trivial names, e.g. weak D type 1, or by their molecular structures, e.g. RHD (V270G). The weak D type 1 was the most frequent known RHD allele (f=1:277) with aberrant coding sequence, exceeding even the $D^{VII}$ allele frequency (Wagner et al. 1997).

Amino acid substitutions in weak D alleles are clustered. The amino acid substitutions observed in weak D types with single missense mutations were not evenly distributed in the RhD protein (FIG. 1). The majority of substitutions occurred in the region of amino acid positions 267 to 397. Single and multiple amino acid substitutions in smaller portions of the RhD protein around positions 2 to 13, 149, and 179 to 225 (weak D type 4 and 14) were also found in weak D alleles. According to the current RhD loop model, the involved amino acids were positioned in the transmembrane and intracellular protein segments.

Normal RhD phenotype controls and RHD promoter. Six control samples with normal RhD phenotype showed a normal RhD protein sequence by RHD specific sequencing of the ten RHD exons. To check for mutations in the RHD promoter, a 675 bp region using primer pair rb13 and rb11d were amplified (Table 2). The promoter region was sequenced using primers re02 and re01 starting at nucleotide position-545 relative to the first nucleotide of the start codon. One sample of each weak D type, DHMi, and $D^{IV}$ type III was employed. No deviation from the published RHD promoter sequence (Huang, 1996) was found.

Statistical evidence that missense mutations can cause weak D phenotypes. The frequency of altered RhD proteins in weak D (158 of 158) and normal D samples (0 of 6) was statistically significantly different (p<0.0001, 2×2 contingency table, Fisher's exact test). A normal RhD coding sequence in the weak D phenotype was expected to occur in less than 1.9% (upper limit of 95% confidence interval, Poisson distribution). It was further excluded that these amino acid substitutions reflected random nucleotide changes only, because of two observations: (i) In the 417 codons of the RHD gene, 2,766 missense and 919 silent mutations may occur. If nucleotide changes in weak D alleles were random, silent mutations were expected with a frequency of 0.249. One silent mutation was observed among a total of 18 mutations in weak D alleles (p=0.039, binomial distribution). Nonsense mutations were assumed to prevent RhD expression (Avent et al. 1997b) and thus excluded from the calculation. (ii) 1,796 bp of the RHD gene were sequenced representing 1,251 bp coding sequence and 545 bp noncoding sequence. If nucleotide changes were random, their occurrence in the noncoding sequence of weak D alleles was expected with a frequency of 0.303. All 18 mutations were, however, located in the coding sequence (p=0.005, binomial distribution).

Haplotype-specific RHD polymorphisms. Introns 3 and 6 were analyzed. To check the RHD intron 3 by RFLP, the 3' part of intron 3 using the RHD specific primer pair rb46 and rb12 was amplified and the PCR products digested with HaeIII. To examine TATT tandem repeats in RHD intron 6, the full length intron 6 using the RHD specific primer pair rf51 and re71 and primer rg62 was amplified used for sequencing.

Polymorphic RHD sequences that differed between the prevalent RHD alleles of the CDe and cDE haplotypes were detected (Table 6). In RHD intron 3, there was a G/C polymorphism that determined a HaeIII-RFLP at position-371 relative to the intron 3/exon 4 junction. In RHD intron 6, there was a variable length TATT tandem repeat starting 1,915 bp 3' of exon 6. In the prevalent RHD allele of the CDe haplotype, the HaeIII, restriction site was present and the TATT repeat region comprised 9 repeats. In the prevalent RHD allele of the cDE haplotype, the HaeIII restriction site was absent and the TATT repeat region comprised 8 repeats. Weak D alleles were identical to the prevalent alleles of the same RH haplotype in regard to these polymorphisms in intron 3 and 6, with the single exception of weak D type 4 that showed 13 TATT repeats. It was concluded that weak D alleles evolved independently in the different RH haplotypes.

TABLE 1

Primers used

| Name | Nucleotide sequence | Genomic region | Position[1] | Strandedness | RHD specific |
|---|---|---|---|---|---|
| ra21 | gtgccacttgacttgggact (SEQ ID NO:1) | intron 2 | 2,823 to 2,842 | sense | no |
| rb7 | atctctccaagcagacccagcaagc (SEQ ID NO:2) | exon 7 | 1,022 to 998 | antisense | no |
| rb11 | tacctttgaattaagcacttcacag (SEQ ID NO:3) | intron 4 | 161 to 185 | sense | yes |
| rb12 | tcctgaacctgctctgtgaagtgc (SEQ ID NO:4) | intron 4 | 198 to 175 | antisense | yes |
| rb13 | ctagagccaaacccacatctcctt (SEQ ID NO:5) | promoter | −675 to −652 | sense | no |
| rb15 | ttattggctacttggtgcc (SEQ ID NO:6) | intron 5 | −612 to −630 | antisense | no |
| rb20d | tcctggctctccctctct (SEQ ID NO:7) | intron 2 | −25 to −8 | sense | yes |
| rb21 | aggtccctcctccagcac (SEQ ID NO:8) | intron 3 | 28 to 11 | antisense | no |
| rb21d | cccaggtccctcctcccagcac (SEQ ID NO:9) | intron 3 | 32 to 11 | antisense | no |
| rb22 | gggagattttttcagccag (SEQ ID NO:10) | intron 4 | 82 to 64 | antisense | no |
| rb24 | agacctttggagcaggagtg (SEQ ID NO:11) | intron 4 | −53 to −34 | sense | no |
| rb25 | agcagggaggatgttacag (SEQ ID NO:12) | intron 5 | −111 to −93 | sense | no |
| rb26 | aggggtgggtagggaatatg (SEQ ID NO:13) | intron 6 | −62 to −43 | sense | no |
| rb44 | gcttgaaatagaagggaaatgggagg (SEQ ID NO:14) | intron 7 | ≈3,000 | antisense | no |
| rb46 | tggcaagaacctggaccttgacttt (SEQ ID NO:15) | intron 3 | −1,279 to −1,255 | sense | no |
| rb52 | ccaggttgttaagcattgctgtacc (SEQ ID NO:16) | intron 7 | ≈−3,300 | sense | yes |
| re01 | atagagaggccagcacaa (SEQ ID NO:17) | promoter | −149 to −132 | sense | yes |
| re02 | tgtaactatgaggagtcag (SEQ ID NO:18) | promoter | −572 to −554 | sense | yes |
| re11d | agaagatgggggaatcttttcct (SEQ ID NO:19) | intron 1 | 129 to 106 | antisense | no |
| re12d | attagccgggcacggtggca (SEQ ID NO:20) | intron 1 | −1,188 to −1,168 | sense | yes |
| re13 | actctaatttcataccaccc (SEQ ID NO:21) | intron 1 | −72 to −53 | sense | no |
| re23 | aaaggatgcaggaggaatgtaggc (SEQ ID NO:22) | intron 2 | 251 to 227 | antisense | no |
| re31 | tgatgaccatcctcaggt (SEQ ID NO:23) | exon 3 | 472 to 455 | antisense | yes |
| re617 | tctcagctcactgcaacctc (SEQ ID NO:24) | intron 6 | 1,998 to 2,017 | sense | no |
| re621 | catcccccttttggtggcc (SEQ ID NO:25) | intron 6 | −102 to −85 | sense | yes |
| re71 | acccagcaagctgaagttgtagcc (SEQ ID NO:26) | exon 7 | 1,008 to 985 | antisense | yes |
| re73 | ccttttttgtccctgatgacc (SEQ ID NO:27) | intron 7 | −67 to −48 | sense | no |

TABLE 1-continued

Primers used

| Name | Nucleotide sequence | Genomic region | Position[1] | Strandedness | RHD specific |
|---|---|---|---|---|---|
| re74 | tatccatgaggtgctgggaac (SEQ ID NO:28) | intron 7 | ≈−200 | sense | no |
| re75 | aaggtaggggctggacag (SEQ ID NO:29) | intron 7 | ≈120 | antisense | yes |
| re82 | aaaaatcctgtgctccaaac (SEQ ID NO:30) | intron 8 | ≈−45 | sense | yes |
| re83 | gagattaaaaatcctgtgctcca (SEQ ID NO:31) | intron 8 | ≈−50 | sense | no |
| re91 | caagagatcaagccaaaatcagt (SEQ ID NO:32) | intron 9 | ≈−40 | sense | no |
| re93 | cacccgcatgtcagactatttggc (SEQ ID NO:33) | intron 9 | ≈300 | antisense | no |
| rf51 | caaaaacccattcttcccg (SEQ ID NO:34) | intron 5 | −332 to −314 | sense | no |
| rg62 | tgtattccaggcagaaggc (SEQ ID NO:35) | intron 6 | 1,736 to 1,755 | sense | no |
| rh5 | gcacagagacggacacag (SEQ ID NO:36) | UTR[2] | −19 to −2 | sense | no |
| rh7 | acgtacaaatgcaggcaac (SEQ ID NO:37) | UTR[2] | 1,330 to 1,313 | antisense | no |
| rr1 | tgttggagagagggggtgatg (SEQ ID NO:38) | UTR | −60 to −41 | sense | no |
| rr3 | cagtctgtgtttaccagatg (SEQ ID NO:39) | UTR | 1,512 to 1,492 | antisense | yes |
| rr4 | agcttactggatgaccacca (SEQ ID NO:40) | UTR | 1,541 to 1,522 | antisense | yes |

[1]The positions of the synthetic oligonucleotides are indicated relative to their distances from the first nucleotide position of the start codon ATG for all primers in the promoter and in the exons including the 3' untranslated part of exon 10, or relative to their adjacent exon/intron boundaries for all other primers. Primer ra21 was reported previously (Poulter et al.1996).
[2]5' UTR: 5' untranslated region of exon 1; UTR: 3' untranslated region of exon 10.

TABLE 2

Sequencing method for all ten RHD exons from genomic DNA

| RHD exon | PCR primers Sense | PCR primers Antisense | RHD specific[2] | PCR conditions[1] Extension | PCR conditions[1] Annealing | Sequencing primers | RHD specific[2] |
|---|---|---|---|---|---|---|---|
| Exon 1 | rb13 | rb11d | no | 10 min | 60° C. | re01 | yes |
| Exon 2 | re12d | re23 | yes | 3 min | 65° C. | re13 | no |
| Exon 3 | ra21 | rb21 | no | 10 min | 60° C. | re31 and rb20d | yes |
| Exon 4 | rb46 | rb12 | yes | 10 min | 60° C. | rb22 | no |
| Exon 5 | rb11 | rh2 | yes | 10 min | 60° C. | rb24 | no |
| Exon 6 | rf51 | re71 | yes | 10 min | 60° C. | rb25 | no |
| Exon 7 | re617 | rb44 | no | 10 min | 60° C. | re621 and re75 | yes |
| Exon 8 | rb52 | rb93 | yes | 10 min | 60° C. | re73 | no |
| Exon 9 | rb52 | rb93 | yes | 10 min | 60° C. | re82/re83 | yes/no |
| Exon 10 | re91 | rr4 | yes | 10 min | 60° C. | rr3/rh7 | yes/no |

[1]Primers were used at a concentration of 1 nM in the Expand High Fidelity PCR System (Boehringer Mannheim, Mannheim, Germany). In the exon 10 PCR, the concentration of MgCl$_2$ was 2.0 nM. Denaturation was 20 s at 92° C., annealing 30 s, elongation temperature 68° C.. Elongation time was increased by 20 s for each cycle after the 10th cycle, except for the re12d/re23 primer pair.
[2]To achieve RHD specificity for genomic nucleotide sequencing, the PCR primer pairs or the sequencing primer or both must not concurrently detect RHCE-derived nucleotide sequences. Primer sequences are given in Table 1.

TABLE 3

PCR-RFLP analysis of five RHD alleles

| Allele | Substitution | PCR primers[1] | | Restriction enzyme |
|---|---|---|---|---|
| RHD(S3C) | 8 C → G | re01 | re11d | SacI |
| RHD(R10Q) | 29 G → A | re01 | re11d | MspI |
| RHD(A149D) | 446 C → A | rb20d | rb21 | AluI |
| RHD(V270G) | 809 T → G | rf51 | re71 | Alw44I |
| RHD(G385A) | 1154 G → C | re82 | re93 | AluI |

[1]Conditions for the rf51/re71 PCR reaction as shown in Table 2. All other PCR reactions were done with non-proofreading Taq-polymerase (Boehringer Mannheim) with 20 s denaturation at 94° C., 30 s annealing at 55° C. and 1 min extension at 72° C. Examples for these PCR-RFLPs of weak D types 1, 2, 3, 5, 6, are shown in FIG. 4.

TABLE 4

Molecular basis of weak RhD phenotypes

| Allele membrane[1] | Effect on Nucleotide change | Exons protein sequence | Predicted localization involved in the cell |
|---|---|---|---|
| RHD(S3C) | C → G at 8 | Ser to Cys at 3 | 1 | IC |
| RHD(R10Q) | G → A at 29 | Arg to Gln at 10 | 1 | IC |
| RHD(W16C, T201R, F223V) | G → C at 48, | Trp to Cys at 16 | 1 | TM |
| | C → G at 602, | Thr to Arg at 201 | 4 | IC |
| | T → G at 667, | Phe to Val at 223 | 5 | TM |
| | G → A at 819 | no change | 6 | — |
| RHD(R114W) | C → T at 340 | Arg to Trp at 114 | 3 | TM |
| RHD(A149D) | C → A at 446 | Ala to Asp at 149 | 3 | TM |
| RHD(S182T, K198N, T201R) | T → A at 544, | Ser to Thr at 182 | 4 | TM |
| | A → T at 594, | Lys to Asn at 198 | 4 | IC |
| | C → G at 602 | Thr to Arg at 201 | 4 | IC |

TABLE 4-continued

Molecular basis of weak RhD phenotypes

| Allele membrane[1] | Effect on Nucleotide change | Exons protein sequence | | Predicted localization involved in the cell |
|---|---|---|---|---|
| RHD(T201R,F223V) | C → G at 602, | Thr to Arg at 201 | 4 | IC |
|  | T → G at 667, | Phe to Val at 223 | 5 | TM |
|  | G → A at 819 | no change | 6 | — |
| RHD(W220R) | T → C at 858 | Trp to Cys at 220 | 5 | TM |
| RHD(V270G) | T → G at 809 | Val to Gly at 270 | 6 | TM |
| RHD(A276P) | G → C at 826 | Ala to Pro at 276 | 6 | TM |
| RHD(G277E) | G → A at 830 | Gly to Glu at 277 | 6 | TM |
| RHD(G282D) | G → A at 845 | Gly to Asp at 282 | 6 | TM |
| RHD(A294P) | G → C at 880 | Ala to Pro at 294 | 6 | TM |
| RHD(M295I) | G → T at 885 | Met to Ile at 295 | 6 | TM |
| RHD(G307R) | G → A at 919 | Gly to Arg at 307 | 6 | IC |
| RHD(G339E) | G → A at 1016 | Gly to Glu at 339 | 7 | TM |
| RHD(G385A) | G → C at 1154 | Gly to Ala at 385 | 9 | TM |
| RHD(W393R) | T → C at 1177 | Trp to Arg at 393 | 9 | IC |
| DHMi | C → T at 848 | Thr to Ile at 283 | 6 | EF |
| D$^{IV}$ type III | RHD-CE (6-9)-D | multiple | 6 to 9 | EF/ TM/ IC |

[1]IC - intracellular, TM - transmembranous, EF - exofacial

TABLE 6

RHD polymorphisms in RHD genes of various haplotypes

| Haplotype[1] | Allele | HaeIII site in intron 3 | TATT-repeat in intron 6 |
|---|---|---|---|
| CDe | prevalent RHD | present | 9 |
| CDe | weak D type 1 | present | 9 |
| CDe | weak D type 3 | present | 9 |
| CDe | weak D type 5 | present | 9 |
| CDe | weak D type 6 | present | 9 |
| CDe | weak D type 7 | present | 9 |
| CDe | weak D type 12 | present | 9 |
| CDe | weak D type 13 | present | 9 |
| CDe | weak D type 17 | N.D. | 9 |
| CDe | D$^{IV}$ type III | present | —[2] |
| cDE | prevalent RHD[3] | absent | 8 |
| cDE | weak D type 2 | absent | 8 |
| cDE | weak D type 8 | absent | 8 |
| cDE | weak D type 9 | absent | 8 |
| cDE | weak D type 10 | absent | 8 |
| cDE | weak D type 14 | absent | 8 |
| cDE | weak D type 15 | absent | 8 |
| cDE | weak D type 16 | absent | 8 |
| cDE | DHMi | absent | 8 |
| c(W16C)De | prevalent RHD | present | 9 |
| c(W16C)De | weak D type 4 | present | 13 |

TABLE 5

Proposed nomenclature for RHD alleles coding for weak D phenotypes and their minimal population frequencies

| Trivial name | Molecular basis (allele) | n[1] | frequency[2] | Phenotype Minimal population frequency[3] phenotype | haplotype |
|---|---|---|---|---|---|
| weak D type 1 | RHD (V270G) | 95 | 70.29% | 0.2964% | 0.003606 (1:277) |
| weak D type 2 | RHD (G385A) | 43 | 18.01% | 0.0759% | 0.000924 (1:1,082) |
| weak D type 3 | RHD (S30) | 7 | 5.19% | 0.0219% | 0.000266 (1:3,759) |
| weak D type 4 | RHD (T201R, F223V) | 6 | 1.30% | 0.0055% | 0.000067 (1:14,925) |
| weak D type 5 | RHD (G307R) | 1 | 0.74% | 0.0031% | 0.000038 (1:26,316) |
| weak D type 6 | RHD (R100) | 1 | 0.74% | 0.0031% | 0.000038 (1:26,316) |
| weak D type 7 | RHD (G339E) | 1 | 0.74% | 0.0031% | 0.000038 (1:26,316) |
| weak D type 8 | RHD (A294P) | 1 | 0.42% | 0.0017% | 0.000021 (1:47,619) |
| weak D type 9 | RHD (A149D) | 1 | 0.42% | 0.0017% | 0.000021 (1:47,619) |
| weak D type 10 | RHD (W393R) | 1 | 0.42% | 0.0018% | 0.000021 (1:47,619) |
| weak D type 11 | RHD (M2951) | 1 | 0.22% | 0.0009% | 0.000011 (1:90,909) |
| weak D type 12 | RHD (G277E) | 0 | — | — | — |
| weak D type 13 | RHD (A276P) | 0 | — | — | — |
| weak D type 14 | RHD (S182T, K198N, T201R) | 0 | — | — | — |
| weak D type 15 | RHD (G282D) | 0 | — | — | — |
| weak D type 16 | RHD (W220R) | 0 | — | — | — |
| weak D type 17 | RHD (R114W) | 0 | — | — | — |
| DHMi | RHD (T2831) | 2 | 0.84% | 0.0035% | 0.000043 (1:23,256) |
| D$^{IV}$ type III | RHD-CE(6-9)-D | 1 | 0.60% | 0.0025% | 0.000031 (1:32,258) |
| Total |  | 161 | 100% | 0.4185% | 0.005094 | weak D type 4 can be subdivided in two forms:
weak D type 4a; see weak D type 4, in the Table
weak D type 4b RHD (W16C, T201R, F223V)
[1]Number of samples observed among 161 blood samples with weak antigen D expression. Types 12 to 17 were not detected among these blood samples, but found independently.
[2]The phenotype frequencies among weak D samples were calculated adjusting for the frequencies of the serologic weak D phenotypes (Wagner et al. 1995). ccDEE weak D samples were assumed to be cDE/cdE.
[3]Phenotype frequencies in the population were calculated from the population frequency of the weak D phenotype in South-Western Germany (Wagner et al. 1995). These are minimal estimates, because some samples with only moderately weakened D expression may have been grouped to normal strength 0. Haplotype frequencies were calculated using a haplotype frequency of 0.411 for RhD negative haplotypes (Wagner et al. 1995) assuming that all weak 0 samples were heterozygous.

TABLE 6-continued

RHD polymorphisms in RHD genes of various haplotypes

| Haplotype[1] | Allele | HaeIII site in intron 3 | TATT-repeat in intron 6 |
|---|---|---|---|
| cDe | prevalent RHD[4] | mostly present | 8 or 9 |
| cDe | weak D type 11 | present | 8 |

[1]The haplotype association of the HaeIII site was tested in 10 CCDee, 8 ccDEE, 10 cc(W16C)De and 10 ccDee samples. The haplotype association of the TATT repeat was tested in 3 CCDee, 3 ccDEE, 1ccDEe, 2 cc(W16C)De and 2 ccDee samples.
[2]Intron 6 derived from RHCE due to a gene conversion.
[3]Six of seven alleles investigated showed 8 repeats, one 9 repeats.
[4]The HaeIII site was present in 8 of 10 samples tested. Samples with HaeIII site showed 9 TATT-repeats, samples without HaeIII site 8 repeats.
N.D. = Not determined

TABLE 7

Predicted localization of RhD protein segments relative to the red blood cells membrane[1]

| Range of amino acids | Intra-cellular | Trans-membranous | Exofacial | Length (amino acids) |
|---|---|---|---|---|
| 1–11 | X | | | 10[2] |
| 12–31 | | X | | 20 |
| 32–53 | | | X | 22 |
| 54–71 | | X | | 18 |
| 72–75 | X | | | 4 |
| 76–93 | | X | | 18 |
| 94–110 | | | X | 17 |
| 111–130 | | X | | 20 |
| 131–134 | X | | | 4 |
| 135–153 | | X | | 19 |
| 154–169 | | | X | 16 |
| 170–187 | | X | | 18 |
| 188–207 | X | | | 20 |
| 208–225 | | X | | 18 |
| 226–238 | | | X | 13 |
| 239–256 | | X | | 18 |
| 257–264 | X | | | 8 |
| 265–282 | | X | | 18 |
| 283–286 | | | X | 4 |
| 287–306 | | X | | 20 |
| 307–333 | X | | | 27 |
| 334–351 | | X | | 18 |
| 352–370 | | | X | 19 |
| 371–388 | | X | | 18 |
| 389–417 | X | | | 29 |
| Total | 5 loops and 2 segments | 12 helices | 6 loops | 416[2] |

[1]Localization of the amino- and carboxyterminal protein end according to Avent et al. {J. Biol. Chem. 1992} and Hermand et al. {Blood 1993}. The transmembranous helices were predicted by PHDhtm {www.embl-heidelberg.de/predictprotein/predictprotein.html}, the helix at positions 371 to 388 by TMpred {ulrec3.unil.ch/software/TMPRED_form.html}.
[2]The amino acid (methionine) at position 1 is not expressed in the mature RhD protein as shown by amino acid sequencing {Avent et al. Biochem. J. 1988}.

TABLE 8

Sample RhD epitope densities for weak D types.

| weak D | RhD epitope density (RhD antigens/red cell) |
|---|---|
| type 3 | 1,500 |
| type 1 | 900 |
| type 2 | 500 |
| type 12 | <100 |

One sample of each weak D type was tested with a polyclonal anti-D (Lorne Laboratories Ltd., Redding, Berkshire, England) as described previously (Flegel and Wagner 1996). Similar results were obtained by monoclonal anti-D (BS228, Biotest AG, Dreieich, Germany; and P3x290, Diagast, Lille, France).

REFERENCES

Agre, P. C., Davies, D. M., Issitt, P. D., Lamy, B. M., Schmidt, P. J., Treacy, M., and Vengelen-Tyler, V. 1992. A proposal to standardize terminology for weak D antigen [Letter]. *Transfusion* 32:86–87.

Arce, M. A., Thompson, E. S., Wagner, S., Coyne, K. E., Ferdman, B. A., and Lublin, D. M. 1993. Molecular cloning of RhD cDNA derived from a gene present in RhD-positive, but not RhD-negative individuals. *Blood* 82:651–655.

Aubin, J. T., Le Van Kim, C., Mouro, I., Colin, Y., Bignozzi, C., Brossard, Y., and Cartron, J. P. 1997. Specificity and sensitivity of RHD genotyping methods by PCR-based DNA amplification. *British Journal of Haematology* 98:356–364.

Avent, N. D., Butcher, S. K., Liu, W., Mawby, W. J., Mallinson, G., Parsons, S. F., Anstee, D. J., Tanner, M. J. 1992. Localization of the C termini of the Rh(rhesus) polypeptides to the cytoplasmic face of the human erythrocyte membrane. *J. Biol. Chem.* 267:15134–15139.

Avent, N. D., Jones, J. W., Liu, W., Scott, M. L., Voak, D., Flegel, W. A., Wagner, F. F., and Green, C. 1997a. Molecular basis of the D variant phenotypes DNU and DII allows localization of critical amino acids required for expression of Rh D epitopes epD3, 4 and 9 to the sixth external domain of the Rh D protein. *British Journal of Haematology* 97:366–371.

Avent, N. D., Martin, P. G., Armstrong-Fisher, S. S., Liu, W., Finning, K. M., Maddocks, D., and Urbaniak, S. J. 1997b. Evidence of genetic diversity underlying Rh D negative, weak D (D'') and partial D phenotypes as determined by multiplex PCR analysis of the RHD gene. *Blood* 89:2568–2577.

Avent, N. D., Rigwell, K., Mawby, W. J., Tanner, M. J., Anstee, D. J., Kumpel, B. 1988. Protein-sequence studies on Rh-related polypeptides suggest the presence of at least two groups of proteins which associate in the human red-cell membrane. *Biochem. J.* 256:1043–1046.

Beckers, E. A., Faas, B. H., Ligthart, P., Overbeeke, M. A., von dem Borne, A. E., van der Schoot, C. E., and van Rhenen, D. J. 1997. Lower antigen site density and weak D immunogenicity cannot be explained by structural genomic abnormalities or regulatory defects of the RHD gene. *Transfusion* 37:616–623.

Beckers, E. A. M., Faas, B. H. W., Overbeeke, M. A. M., von dem Borne, A. E. G. K., van Rhenen, D. J., and van der Schoot, C. E. 1995. Molecular aspects of the weak-D phenotype. *Transfusion* 35:50S Bowman, J. M. 1998. RhD hemolytic disease of the newborn. *N. Engl. J. Med.* 339:1775–1777

Cartron, J.-P. 1996. Rh DNA—coordinator's report. *Transfusion Clinique et Biologique* 3:491–495.

Ceppellini, R., Dunn, L. C., and Turry, M. 1955. An interaction between alleles at the Rh locus in man which weakens the reactivity of the Rho factor (D$^u$). *Proceedings of the National Academy of Sciences U.S.A.* 41:283–288.

Cherif-Zahar, B., Raynal, V., Gane, P., Mattei, M. G., Bailly, P., Gibbs, B., Colin, Y., and Cartron, J.-P. 1996. Candidate gene acting as a suppressor of the RH locus in most cases of Rh-deficiency. *Nature Genetics* 12:168–173.

Flegel, W. A., Müller, T. H., Schunter, F., Gassner, C., Schönitzer, D., and Wagner, F. F. 1997. D category VI type III: A D-Ce(3–6)-D hybrid protein with normal RhD antigen density on red cells [Abstract]. *Transfusion* 37S: 101S Flegel, W. A. and Wagner, F. F. 1996. RHD epitope density profiles of RHD variant red cells analyzed by flow cytometry. *Transfusion Clinique et Biologique* 3:429–431.

Fukumori, Y., Hori, Y., Ohnoki, S., Nagao, N., Shibata, H., Okubo, Y., and Yamaguchi, H. 1997. Further analysis of Del (D-elute) using polymerase chain reaction (PCR) with RHD gene-specific primers. *Transfusion Medicine* 7:227–231.

Gassner, C., Schmarda, A., Kilga-Nogler, S., Jenny-Feldkircher, B., Rainer, E., Müller, T. H., Wagner, F. F., Flegel, W. A., and Schönitzer, D. 1997. RhesusD/CE typing by polymerase chain reaction using sequence-specific primers. *Transfusion* 37:1020–1026.

Hasekura, H., Ota, M., Ito, S., Hasegawa, Y., Ichinose, A., Fukushima, H., and Ogata, H. 1990. Flow cytometric studies of the D antigen of various Rh phenotypes with particular reference to D$^u$ and D$^{el}$. *Transfusion* 30:236–238.

Hermand, P., Mouro, I., Huet, M., Bloy, C., Suyama, K., Goldstein, J., Cartron, J. P., Bailly, P. 0.1993. Immunochemical characterization of rhesus proteins with antibodies raised against synthetic peptides. *Blood* 82:669–676.

Huang, C. H. 1996. Alteration of RH gene structure and expression in human dCCee and DCW-red blood cells: phenotypic homozygosity versus genotypic heterozygosity. *Blood* 88:2326–2333.

Huang, C. H. 1997. Molecular insights into the Rh protein family and associated antigens. *Current Opinion in Hematology* 4:94–103.

Huang, C. H., Chen, Y., and Reid, M. 1997. Human D(IIIa) erythrocytes: RhD protein is associated with multiple dispersed amino acid variations. *Am. J. Hematol.* 55:139–145.

Issitt, P. D. and Telen, M. J. 1996. D, weak D (DU), and partial D: the molecular story unfolds. *Transfusion* 36:97–100.

Jones, J. W., Finning, K. M., Mattock, R., Voak, D., Scott, M. L., and Avent, N. D. 1997. The serological profile and molecular basis of a new partial D phenotype, DHR. *Vox Sanguinis* 73:252–256.

Jones, J. W., Lloyd-Evans, P., and Kumpel, B. M. 1996. Quantitation of Rh D antigen sites on weak D and D variant red cells by flow cytometry. *Vox Sanguinis* 71:176–183.

Kajii, E., Umenishi, F., Omi, T., and Ikemoto, S. 1995. Intricate combinatorial patterns of exon splicing generate multiple Rh-related isoforms in human erythroid cells. *Human Genetics* 95:657–665.

Kemp, T. J., Poulter, M., and Carritt, B. 1996. A recombination hot spot in the Rh genes revealed by analysis of unrelated donors with the rare D-phenotype. *American Journal of Human Genetics* 59:1066–1073.

Le Van Kim, C., Mouro, I., Cherif-Zahar, B., Raynal, V., Cherrier, C., Cartron, J. P., and Colin, Y. 1992. Molecular cloning and primary structure of the human blood group RhD polypeptide. *Proceedings of the National Academy of Sciences U.S.A.* 89:10925–10929.

Leader, K. A., Kumpel, B. M., Poole G. D., Kirkwood, J. T., Merry A. H. and Bradley, B. A. 1990. Human monoclonal anti-D with reactivity against category DVI cells used in blood grouping and determination of the incidence of the category DVI phenotype in the DU population. *Vox Sang* 58:(2):106–11

Legler, T. J., Blaschke, V., Bustami, N., Malekan, M., Schwartz, D. W. M., Mayr, W. R., Panzer, S., and Köhler, M. 1997. RHD genotyping on exons 2, 5, 7, intron 4 and the 3' non-coding region in D$^{weak}$, D$^{VI}$, DFR and D-individuals. *Transfusion* 37:100S Liu, W., Jones, J. W., Scott, M. L., Voak, D., and Avent, N. D. 1996. Molecular analysis of two D-variants, D$^{HMi}$ and D$_{HMii}$ [Abstract]. *Transfusion Medicine* 6(suppl 2):21

Lomas, C., Grässmann, W., Ford, D., Watt, J., Gooch, A., Jones, J., Beolet, M., Stern, D., Wallace, M., and Tippett, P. 1994. FPTT is a low-incidence Rh antigen associated with a "new" partial Rh D phenotype, DFR. *Transfusion* 34:612–616.

Lomas, C., McColl, K., and Tippett, P. 1993. Further complexities of the Rh antigen D disclosed by testing category D$^{II}$ cells with monoclonal anti-D. *Transfusion Medicine* 3:67–69.

Lomas, C., Tippett, P., Thompson, K. M., Melamed, M. D., and Hughes-Jones, N. C. 1989. Demonstration of seven epitopes on the Rh antigen D using human monoclonal anti-D antibodies and red cells from D categories. *Vox Sanguinis* 57:261–264.

Mollison, P. L., Engelfriet, C. P., and Contreras, M. 1993. *Blood transfusion in clinical medicine.* 9th ed. London: Blackwell Scientific Publications.

Moore, B. P. L. 1984. Does knowledge of D$^u$ status serve a useful purpose? *Vox Sanguinis* 46S1:95–97.

Mourant, A. E., Kopec, A. C., and Domaniewska-Sobczak, K. 1976. *The distribution of the human blood groups and other polymorphisms.* 2nd ed. London: Oxford University Press.

Nelson, M., Barrow, L. A., Popp, H., and Gibson, J. 1995. Some observations on D antigen expression of D-positive and 'weak D-positive' red cells as assessed by flow cytometry. *Vox Sanguinis* 69:152–154.

Nicholson, G., Lawrence, A., Ala, F. A., and Bird, G. W. G. 1991. Semi-quantitative assay of D antigen site density by flow cytometric analysis. *Transfusion Medicine* 1:87–90.

Poulter, M., Kemp, T. J., and Carritt, B. 1996. DNA-based Rhesus typing: simultaneous determination of RHC and RHD status using the polymerase chain reaction. *Vox Sanguinis* 7:164–168.

Roubinet, F., Apoil, P. A., and Blancher, A. 1996. Frequency of partial D phenotypes in the south western region of France. *Transfusion Clinique et Biologique* 3:247–255.

Rouillac, C., Gane, P., Cartron, J.-P., Le Pennec, P. Y., and Colin, Y. 1996. Molecular basis of the altered antigenic expression of RhD in weak D (D$^u$) and RhC/e in R$^N$ phenotypes. *Blood* 87:4853–4861.

Rouillac, C., Le Van Kim, C., Beolet, M., Cartron, J. P., and Colin, Y. 1995. Leu110Pro substitution in the RhD polypeptide is responsible for the D$^{VII}$ category blood group phenotype. *American Journal of Hematology* 49:87–88.

Salmon, C., Cartron, J.-P., and Rouger, P. 1984. *The human blood groups.* New York: Masson.

Scott, M. 1996. Rh serology—coordinator's report. *Transfusion Clinique et Biologique* 3:333–337.

Siegel, D. L., Silberstein, L. E. 1994. Expression and characterization of recombinant anti-Rh(D) antibodies on filamentous phage: a model system for isolating human red blood cell antibodies by repertoire cloning. *Blood Apr.* 15:83(8):2334–44

Stratton, F. 1946. A new Rh allelomorph. *Nature* 158:25

Tazzari, P. L., Bontadini, A., Belletti, D., Malferrari, F., and Conte, R. 1994. Flow cytometry: a tool in immunohematology for D+$^w$ (D$^u$) antigen evaluation? *Vox Sanguinis* 67:382–386.

Tippett, P. and Sanger, R. 1962. Observations on subdivisions of Rh antigen D. *Vox Sanguinis* 7:9–13.

Tippett, P. and Sanger, R. 1977. Further observations on subdivisions of the Rh antigen D. *Das Ärztliche Laboratorium* 23:476–480.

Wagner, F. F. 1994. Influence of Rh phenotype on the antigen density of C, c, and D: flow cytometric study using a frozen standard red cell. *Transfusion* 34:671–676.

Wagner, F. F., Hillesheim, B., and Flegel, W. A. 1997. D-Kategorie VII beruht einheitlich auf der Aminosäuresubstitution Leu(110)Pro. *Beiträge zur Infusionstherapie und Transfusionsmedizin* 34:220–223.

Wagner, F. F., Kasulke, D., Kerowgan, M., and Flegel, W. A. 1995. Frequencies of the blood groups ABO, Rhesus, D category VI, Kell, and of clinically relevant high-frequency antigens in South-Western Germany. *Infusionstherapie und Transfusionsmedizin* 22:285–290.

Wissenschaftlicher Beirat der Bundesärztekammer and Bundesgesundheitsamt. 1992. *Richtlinien zur Blutgruppenbestimmung und Bluttransfusion.* Köln: Deutscher Ärzte-Verlag.

---

The invention claimed is:

1. An isolated nucleic acid molecule encoding a human Rhesus D antigen contributing to or indicative of the weak D phenotype, said nucleic acid molecule carrying at least one missense mutation, as compared to wild type Rhesus D antigen set forth as SEQ ID NO:41, wherein the missense mutation encodes an amino acid substitution selected from any of the following: in position 3 is from Ser to Cys, in position 10 from Arg to Gln, in position 16 from Trp to Cys, in position 114 from Arg to Trp, in position 149 from Ala to Asp, in position 182 from Ser to Thr, in position 198 from Lys to Asn, in position 201 from Thr to Arg, in position 220 from Trp to Arg, in position 223 from Phe to Val, in position 270 from Val to Gly, in position 276 from Ala to Pro, in position 277 from Gly to Glu, in position 282 from Gly to Asp, in position 294 from Ala to Pro, in position 295 from Met to Ile, in position 307 from Gly to Arg, in position 339 from Gly to Glu, in position 385 from Gly to Ala and in position 393 from Trp to Arg of the amino acid sequence encoded by SEQ ID NO:41 (FIG. 2), or a combination of said substitutions.

2. An isolated nucleic acid molecule encoding a human Rhesus D antigen contributing to or indicative of the weak D phenotype, said nucleic acid molecule carrying at least one missense mutation, as compared to wild type Rhesus D antigen set forth as SEQ ID NO:41, wherein said missense mutation is selected from any of the following with reference to SEQ ID NO:41: in position 8 is from C to G, in position 29 from G to A, in position 48 from G to C, in position 340 from C to T, in position 446 from C to A, in position 544 from T to A, in position 594 from A to T, in position 602 from C to G, in position 658 from T to C, in position 667 from T to G, in position 809 from T to G, in position 819 from G to A, in position 826 from G to C, in position 830 from G to A, in position 845 from G to A, in position 880 from G to C, in position 885 from G to T, in position 919 from G to A, in position 1016 from G to A, in position 1154 from G to C and in position 1177 from T to C, or a combination of said missense mutations.

3. The nucleic acid molecule of claim 2 wherein said combination of missense mutations is selected from any of the following with reference to SEQ ID NO:41: positions 544, 594 and 602 and is T to A at position 544, A to T at position 594 and C to G at position 602 or comprises positions 602, 667 and 819 and is C to G at position 602, T to G at position 667 and G to A at position 819 or comprises positions 48, 602, 667 and 819 and is G to C at position 48, C to G at position 602, T to G at position 667 and G to A at position 819.

4. The nucleic acid molecule of any one of claim 1, 2, or 3 wherein said molecule is mRNA or genomic DNA.

5. A vector comprising the nucleic acid molecule of any one of claim 1, 2, or 3.

6. An isolated host cell transformed with the vector of claim 5, wherein the host cell is selected from a bacterial cell, yeast cell, fungal cell and insect cell.

7. A method of producing a Rhesus D antigen contributing to the weak D phenotype comprising culturing the host cell of claim 6 under suitable conditions and isolating the Rhesus D antigen produced.

8. A kit comprising the isolated nucleic acid of any of claim 1, 2, or 3.

9. The nucleic acid molecule of claim 1, wherein said combination of substitutions is selected from one or more of the following:

positions 182 is from S to T, 198 from K to N, and 201 from T to R; positions 201 is from T to R and 223 from F to V; or in positions 16 is from W to C, 201 from T to R, and 223 from F to Y of the amino acid sequence encoded by SEQ ID NO:41 (FIG. 2).

10. An isolated host cell transformed with the vector of claim 5, wherein said host cell is suitable for assessment of anti-Rhesus D antibody affinity, avidity, reactivity or specificity.

* * * * *

SEQUENCE LISTING

<160> NUMBER OF SEQ ID NOS: 43

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
gtgccacttg acttgggact     20

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide

<400> SEQUENCE: 2
atctctccaa gcagacccag caagc     25

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide

<400> SEQUENCE: 3
tacctttgaa ttaagcactt cacag     25

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide

<400> SEQUENCE: 4
tcctgaacct gctctgtgaa gtgc     24

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide

<400> SEQUENCE: 5

```
ctagagccaa acccacatct cctt                                          24
```

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide

<400> SEQUENCE: 6

```
ttattggcta cttggtgcc                                                19
```

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide

<400> SEQUENCE: 7

```
tcctggctct ccctctct                                                 18
```

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide

<400> SEQUENCE: 8

```
aggtccctcc tccagcac                                                 18
```

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide

<400> SEQUENCE: 9

```
cccaggtccc tcctcccagc ac                                            22
```

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide

<400> SEQUENCE: 10

```
gggagatttt ttcagccag                                                19
```

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11

```
agacctttgg agcaggagtg                                               20
```

<210> SEQ ID NO 12
<211> LENGTH: 19
<212> TYPE: DNA
<213> ORGANISM: Artificial Sequence

```
<220> FEATURE:
<223> OTHER INFORMATION: Oligonucleotide

<400> SEQUENCE: 12
agcagggagg atgttacag                                                    19

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
aggggtgggt agggaatatg                                                   20

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide

<400> SEQUENCE: 14
gcttgaaata gaagggaaat gggagg                                            26

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide

<400> SEQUENCE: 15
tggcaagaac ctggaccttg acttt                                             25

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide

<400> SEQUENCE: 16
ccaggttgtt aagcattgct gtacc                                             25

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide

<400> SEQUENCE: 17
atagagaggc cagcacaa                                                     18

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide

<400> SEQUENCE: 18
tgtaactatg aggagtcag                                                    19
```

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide

<400> SEQUENCE: 19
agaagatggg ggaatctttt tcct                                    24

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide

<400> SEQUENCE: 20
attagccggg cacggtggca                                         20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide

<400> SEQUENCE: 21
actctaattt cataccaccc                                         20

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide

<400> SEQUENCE: 22
aaaggatgca ggaggaatgt aggc                                    24

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide

<400> SEQUENCE: 23
tgatgaccat cctcaggt                                           18

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide

<400> SEQUENCE: 24
tctcagctca ctgcaacctc                                         20

<210> SEQ ID NO 25
<211> LENGTH: 18
<212> TYPE: DNA
<213> ORGANISM: Artificial Sequence
<220> FEATURE:
<223> OTHER INFORMATION: Oligonucleotide -continued

```
<400> SEQUENCE: 25
catccccctt tggtggcc                                                18

<210> SEQ ID NO 26
<211> LENGTH: 24
<212> TYPE: DNA
<213> ORGANISM: Artificial Sequence
<220> FEATURE:
<223> OTHER INFORMATION: Oligonucleotide

<400> SEQUENCE: 26
acccagcaag ctgaagttgt agcc                                         24

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide

<400> SEQUENCE: 27 ccttttttgtc cctgatgacc                                             20

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide

<400> SEQUENCE: 28
tatccatgag gtgctgggaa c                                            21

<210> SEQ ID NO 29
<211> LENGTH: 18
<212> TYPE: DNA
<213> ORGANISM: Artificial Sequence
<220> FEATURE:
<223> OTHER INFORMATION: Oligonucleotide

<400> SEQUENCE: 29
aaggtagggg ctggacag                                                18

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
aaaaatcctg tgctccaaac                                              20

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide

<400> SEQUENCE: 31
gagattaaaa atcctgtgct cca                                          23

<210> SEQ ID NO 32
```

```
<211> LENGTH: 23
<212> TYPE: DNA
<213> ORGANISM: Artificial Sequence
<220> FEATURE:
<223> OTHER INFORMATION: Oligonucleotide

<400> SEQUENCE: 32
caagagatca agccaaaatc agt                                        23

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide

<400> SEQUENCE: 33
cacccgcatg tcagactatt tggc                                       24

<210> SEQ ID NO 34
<211> LENGTH: 19
<212> TYPE: DNA
<213> ORGANISM: Artificial Sequence
<220> FEATURE:
<223> OTHER INFORMATION: Oligonucleotide

<400> SEQUENCE: 34
caaaaaccca ttcttcccg                                             19

<210> SEQ ID NO 35
<211> LENGTH: 19
<212> TYPE: DNA
<213> ORGANISM: Artificial Sequence
<220> FEATURE:
<223> OTHER INFORMATION: Oligonucleotide

<400> SEQUENCE: 35
tgtattccag gcagaaggc                                             19

<210> SEQ ID NO 36
<211> LENGTH: 18
<212> TYPE: DNA
<213> ORGANISM: Artificial Sequence
<220> FEATURE:
<223> OTHER INFORMATION: Oligonucleotide

<400> SEQUENCE: 36
gcacagagac ggacacag                                              18

<210> SEQ ID NO 37
<211> LENGTH: 19
<212> TYPE: DNA
<213> ORGANISM: Artificial Sequence
<220> FEATURE:
<223> OTHER INFORMATION: Oligonucleotide

<400> SEQUENCE: 37
acgtacaaat gcaggcaac                                             19

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
```

-continued

```
tgttggagag agggtgatg                                              20

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide

<400> SEQUENCE: 39
cagtctgttg tttaccagat g                                           21

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
agcttactgg atgaccacca                                             20

<210> SEQ ID NO 41
<211> LENGTH: 1254
<212> TYPE: DNA
<213> ORGANISM: Homosapien
<220> FEATURE:
<221> NAME/KEY: CDS
<222> LOCATION: (1)...(1251)

<400> SEQUENCE: 41 atg agc tct aag tac ccg cgg tct gtc cgg cgc tgc ctg ccc ctc tgg     48
Met Ser Ser Lys Tyr Pro Arg Ser Val Arg Arg Cys Leu Pro Leu Trp
 1               5                  10                  15 gcc cta aca ctg gaa gca gct ctc att ctc ctc ttc tat ttt ttt acc     96
Ala Leu Thr Leu Glu Ala Ala Leu Ile Leu Leu Phe Tyr Phe Phe Thr
             20                  25                  30 cac tat gac gct tcc tta gag gat caa aag ggg ctc gtg gca tcc tat    144
His Tyr Asp Ala Ser Leu Glu Asp Gln Lys Gly Leu Val Ala Ser Tyr
         35                  40                  45 caa gtt ggc caa gat ctg acc gtg atg gcg gcc att ggc ttg ggc ttc    192
Gln Val Gly Gln Asp Leu Thr Val Met Ala Ala Ile Gly Leu Gly Phe
     50                  55                  60 ctc acc tcg agt ttc cgg aga cac agc tgg agc agt gtg gcc ttc aac    240
Leu Thr Ser Ser Phe Arg Arg His Ser Trp Ser Ser Val Ala Phe Asn
 65                  70                  75                  80 ctc ttc atg ctg gcg ctt ggt gtg cag tgg gca atc ctg ctg gac ggc    288
Leu Phe Met Leu Ala Leu Gly Val Gln Trp Ala Ile Leu Leu Asp Gly
                 85                  90                  95 ttc ctg agc cag ttc cct tct ggg aag gtg gtc atc aca ctg ttc agt    336
Phe Leu Ser Gln Phe Pro Ser Gly Lys Val Val Ile Thr Leu Phe Ser
            100                 105                 110 att cgg ctg gcc acc atg agt gct ttg tcg gtg ctg atc tca gtg gat    384
Ile Arg Leu Ala Thr Met Ser Ala Leu Ser Val Leu Ile Ser Val Asp
        115                 120                 125 gct gtc ttg ggg aag gtc aac ttg gcg cag ttg gtg gtg atg gtg ctg    432
Ala Val Leu Gly Lys Val Asn Leu Ala Gln Leu Val Val Met Val Leu
    130                 135                 140 gtg gag gtg aca gct tta ggc aac ctg agg atg gtc atc agt aat atc    480
Val Glu Val Thr Ala Leu Gly Asn Leu Arg Met Val Ile Ser Asn Ile
145                 150                 155                 160 ttc aac aca gac tac cac atg aac atg atg cac atc tac gtg ttc gca    528
```

-continued

| | | | | | | | | | | | | | | | |
|---|---|---|---|---|---|---|---|---|---|---|---|---|---|---|---|
| Phe | Asn | Thr | Asp | Tyr | His | Met | Asn | Met | Met | His | Ile | Tyr | Val | Phe | Ala |
| | | | 165 | | | | 170 | | | | | 175 | | | |

```
gcc tat ttt ggg ctg tct gtg gcc tgg tgc ctg cca aag cct cta ccc      576
Ala Tyr Phe Gly Leu Ser Val Ala Trp Cys Leu Pro Lys Pro Leu Pro
            180                 185                 190 gag gga acg gag gat aaa gat cag aca gca acg ata ccc agt ttg tct      624
Glu Gly Thr Glu Asp Lys Asp Gln Thr Ala Thr Ile Pro Ser Leu Ser
            195                 200                 205 gcc atg ctg ggc gcc ctc ttc ttg tgg atg ttc tgg cca agt ttc aac      672
Ala Met Leu Gly Ala Leu Phe Leu Trp Met Phe Trp Pro Ser Phe Asn
    210                 215                 220 tct gct ctg ctg aga agt cca atc gaa agg aag aat gcc gtg ttc aac      720
Ser Ala Leu Leu Arg Ser Pro Ile Glu Arg Lys Asn Ala Val Phe Asn
225                 230                 235                 240 acc tac tat gct gta gca gtc agc gtg gtg aca gcc atc tca ggg tca      768
Thr Tyr Tyr Ala Val Ala Val Ser Val Val Thr Ala Ile Ser Gly Ser
                245                 250                 255 tcc ttg gct cac ccc caa ggg aag atc agc aag act tat gtg cac agt      816
Ser Leu Ala His Pro Gln Gly Lys Ile Ser Lys Thr Tyr Val His Ser
            260                 265                 270 gcg gtg ttg gca gga ggc gtg gct gtg ggt acc tcg tgt cac ctg atc      864
Ala Val Leu Ala Gly Gly Val Ala Val Gly Thr Ser Cys His Leu Ile
            275                 280                 285 cct tct ccg tgg ctt gcc atg gtg ctg ggt ctt gtg gct ggg ctg atc      912
Pro Ser Pro Trp Leu Ala Met Val Leu Gly Leu Val Ala Gly Leu Ile
        290                 295                 300 tcc gtc ggg gga gcc aag tac ctg ccg ggg tgt tgt aac cga gtg ctg      960
Ser Val Gly Gly Ala Lys Tyr Leu Pro Gly Cys Cys Asn Arg Val Leu
305                 310                 315                 320 ggg att ccc cac agc tcc atc atg ggc tac aac ttc agc ttg ctg ggt     1008
Gly Ile Pro His Ser Ser Ile Met Gly Tyr Asn Phe Ser Leu Leu Gly
                325                 330                 335 ctg ctt gga gag atc atc tac att gtg ctg ctg gtg ctt gat acc gtc     1056
Leu Leu Gly Glu Ile Ile Tyr Ile Val Leu Leu Val Leu Asp Thr Val
            340                 345                 350 gga gcc ggc aat ggc atg att ggc ttc cag gtc ctc ctc agc att ggg     1104
Gly Ala Gly Asn Gly Met Ile Gly Phe Gln Val Leu Leu Ser Ile Gly
        355                 360                 365 gaa ctc agc ttg gcc atc gtg ata gct ctc acg tct ggt ctc ctg aca     1152
Glu Leu Ser Leu Ala Ile Val Ile Ala Leu Thr Ser Gly Leu Leu Thr
370                 375                 380 ggt ttg ctc cta aat ctt aaa ata tgg aaa gca cct cat gag gct aaa     1200
Gly Leu Leu Leu Asn Leu Lys Ile Trp Lys Ala Pro His Glu Ala Lys
385                 390                 395                 400 tat ttt gat gac caa gtt ttc tgg aag ttt cct cat ttg gct gtt gga     1248
Tyr Phe Asp Asp Gln Val Phe Trp Lys Phe Pro His Leu Ala Val Gly
                405                 410                 415 ttt taa                                                              1254
Phe
```

<210> SEQ ID NO 42
<211> LENGTH: 700
<212> TYPE: DNA
<213> ORGANISM: Homosapien

<400> SEQUENCE: 42

```
agccacttca acgttttgag tctcagtggc ctcatctgta aagtgagaat taagagatgg       60
tgcatgtaaa gtgcttaacg gggagtaaat ggtaggcaaa cattagctgc tgctattagt      120
acagagagac aatggtgtgt gtgagtcttg tgggcagaga tgggtgagag gggagacaaa      180
```

```
acaagttctc atgatgatgg gggcagggyg tccagctggt ggtgtcggag ggaagtctgg      240
acagaccagt ggtggggctc gggtgggagg cactgggggg gctggagtgg aaagaatgtg      300
gccacagatg acagcttcac agcagaattc agtgctaaga ggaagtgagt ggccatgagt      360
tccatggtga cagaaagtct aagacaccta gcaaggcagg agtgggtgtc agctcaggga      420
agctcagagg ctaaacctag gtgagagctg agggtgtcag ataagagcaa ggcaaggctc      480
cggttctgga gtagtgaagg acatagcaga gctataaccc aggaacaagg cccagcttat      540
tggaactggg accagtcaca cagggtggca caggcaccaa gtagccaata ataataataa      600
aaacaataac aatgatttat gtctattggg catttattca tgttctatgc cagacactgg      660
actaagagct ttatatgtgg aaactcattt aatccttaca                            700

<210> SEQ ID NO 43
<211> LENGTH: 700
<212> TYPE: DNA
<213> ORGANISM: Homosapien

<400> SEQUENCE: 43
agccacttca acgttttgag tctcagtggc ctcatctgta aagtgggaat taagagatgg       60
tgcatgtaaa gtgcttaacg gggagtaaat ggtaggcaaa cattagctgc tgctattagt      120
aaagagagac gatggtgtgt gtgagtcttg tgggcagaga tgggtgagag gggagacaaa      180
acaagttctc atgatgatgg gggaaggggc tccagctggt ggtgtcggag ggaagtctgg      240
acagaccagt ggtggggctc gggtgggagg cactgggggg gctggagtgg aaagaatgtg      300
gccacagatg acagcttcac agcagaattc agtgctaaga ggaagtgagt ggccatgagt      360
tccatggtga cagaaagtct aagacaccca gcaaggcagg agtgggtgtc aactcaggga      420
agcccagagg ctaatcctag gtgagagctg agggtgtcag ataagagcaa ggcaaggctc      480
cggttctgga gcagtgaagg acatagcaga gctatgaccc aggaacaagg cccagcttat      540
tgaaactggg cccagtcaca cagggtggca caggcaccaa gtagccaata ataataataa      600
aaacaataac aatgatttgt gtctactggg catttattca tgttctatgc cagacactgg      660
gctaagagct ttatatgtgg aaactcattt aatccttaca                            700
```